(12) United States Patent
Grainger et al.

(10) Patent No.: US 6,365,215 B1
(45) Date of Patent: Apr. 2, 2002

(54) ORAL SENSORY PERCEPTION-AFFECTING COMPOSITIONS CONTAINING DIMETHYL SULFOXIDE, COMPLEXES THEREOF AND SALTS THEREOF

(75) Inventors: Brian T. Grainger, Montgomery Township; Robert J. Kleinhenz, Perrineville; Gary W. Christensen, Neptune, all of NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/710,452

(22) Filed: Nov. 9, 2000

(51) Int. Cl.[7] .................................................. A61K 9/20
(52) U.S. Cl. ........................................................ 426/535
(58) Field of Search ........................... 549/89; 426/535, 426/590; 424/439, 440, 441, 48, 49

(56) References Cited

U.S. PATENT DOCUMENTS 4,353,896 A * 10/1982 Levy ........................... 424/195
5,753,270 A * 5/1998 Beauchamp et al. ......... 424/667
6,197,334 B1 * 3/2001 Renda .......................... 424/464

* cited by examiner

Primary Examiner—James H. Reamer
(74) Attorney, Agent, or Firm—Joseph F. Leightner

(57) ABSTRACT

Described are oral sensory perception-affecting compositions containing dimethyl sulfoxide, complexes thereof and salts thereof, specifically:

(i) dimethyl sulfoxide; and
(ii) a second compound or group of compounds:
  (a) containing at least one menthyl moiety; and/or
  (b) containing at least one vanillyl moiety; and/or
  (c) containing at least one carboxamide moiety when the weight ratio of "second compound(s)":dimethyl sulfoxide, is in the range of from about 1,000:1 down to about 3:10 and food grade acceptable salts thereof. Also described are oral sensory perception-affecting (e.g., "coolant")-imparting consumable articles (e.g., mouthwashes and the like) comprising a consumable article base and at least one of the aforementioned oral sensory perception-affecting compositions. Also described are complexes of (i) dimethyl sulfoxide and (ii) at least one of the aforementioned second compounds or group(s) of compounds.

6 Claims, 17 Drawing Sheets

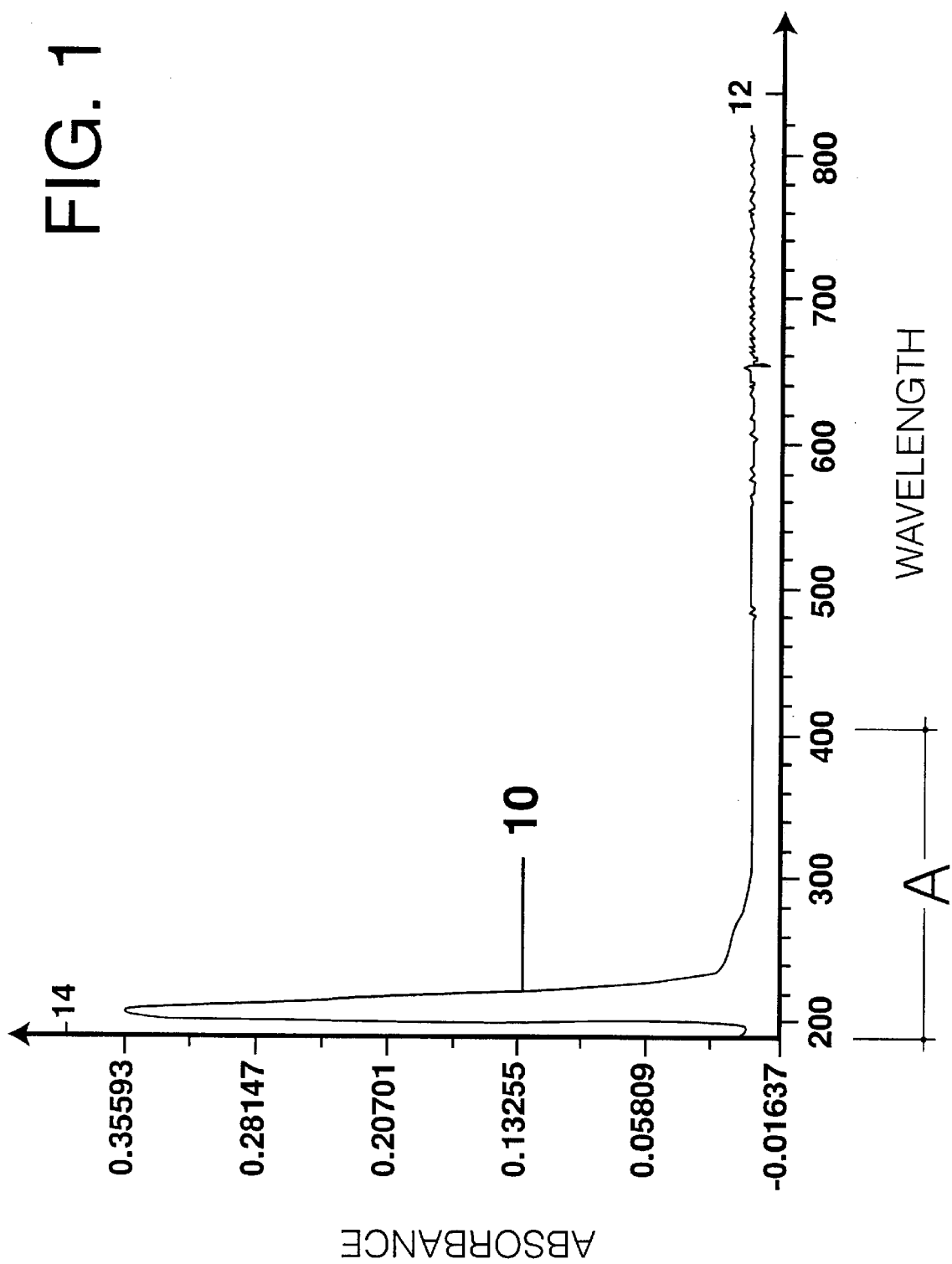

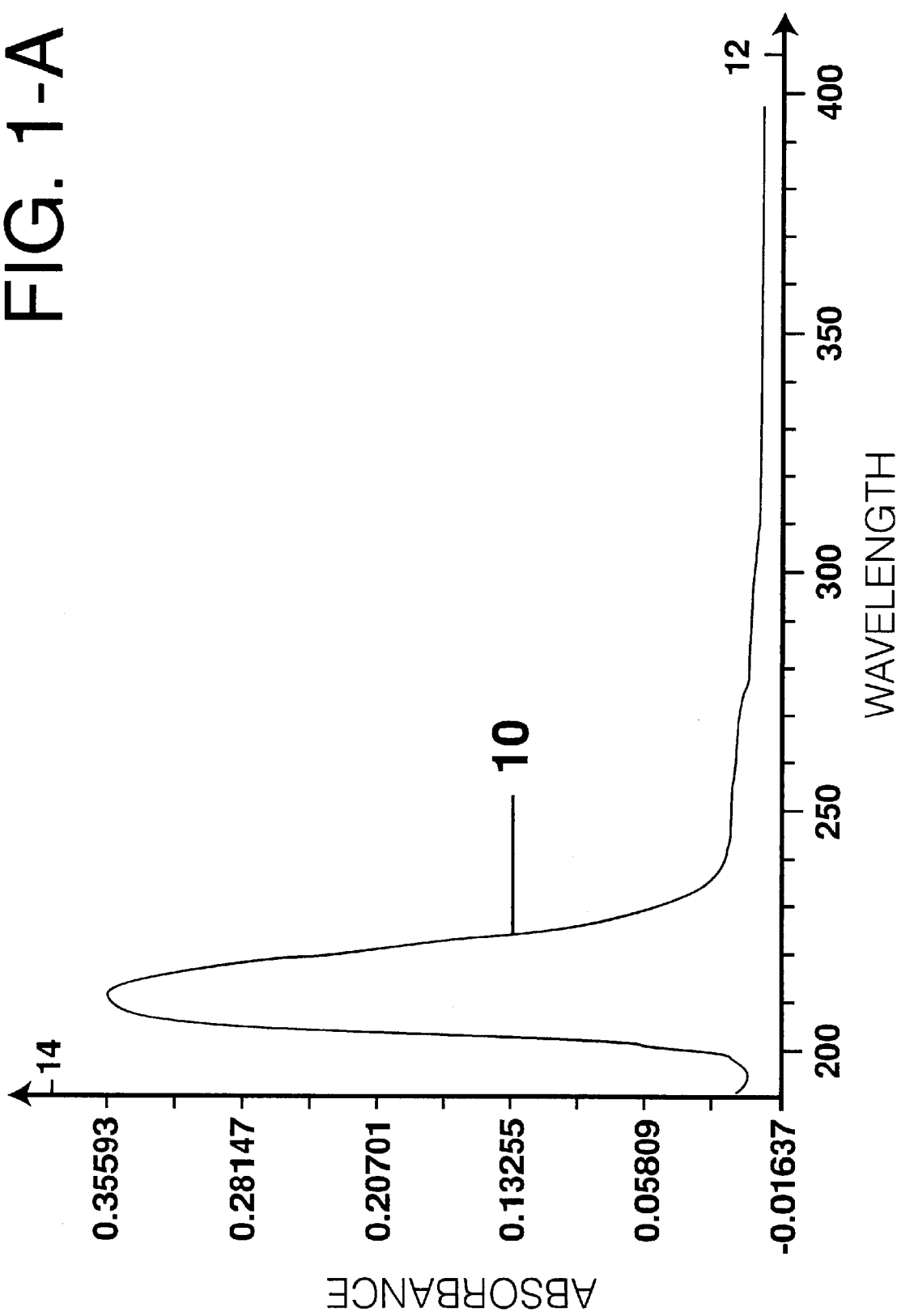

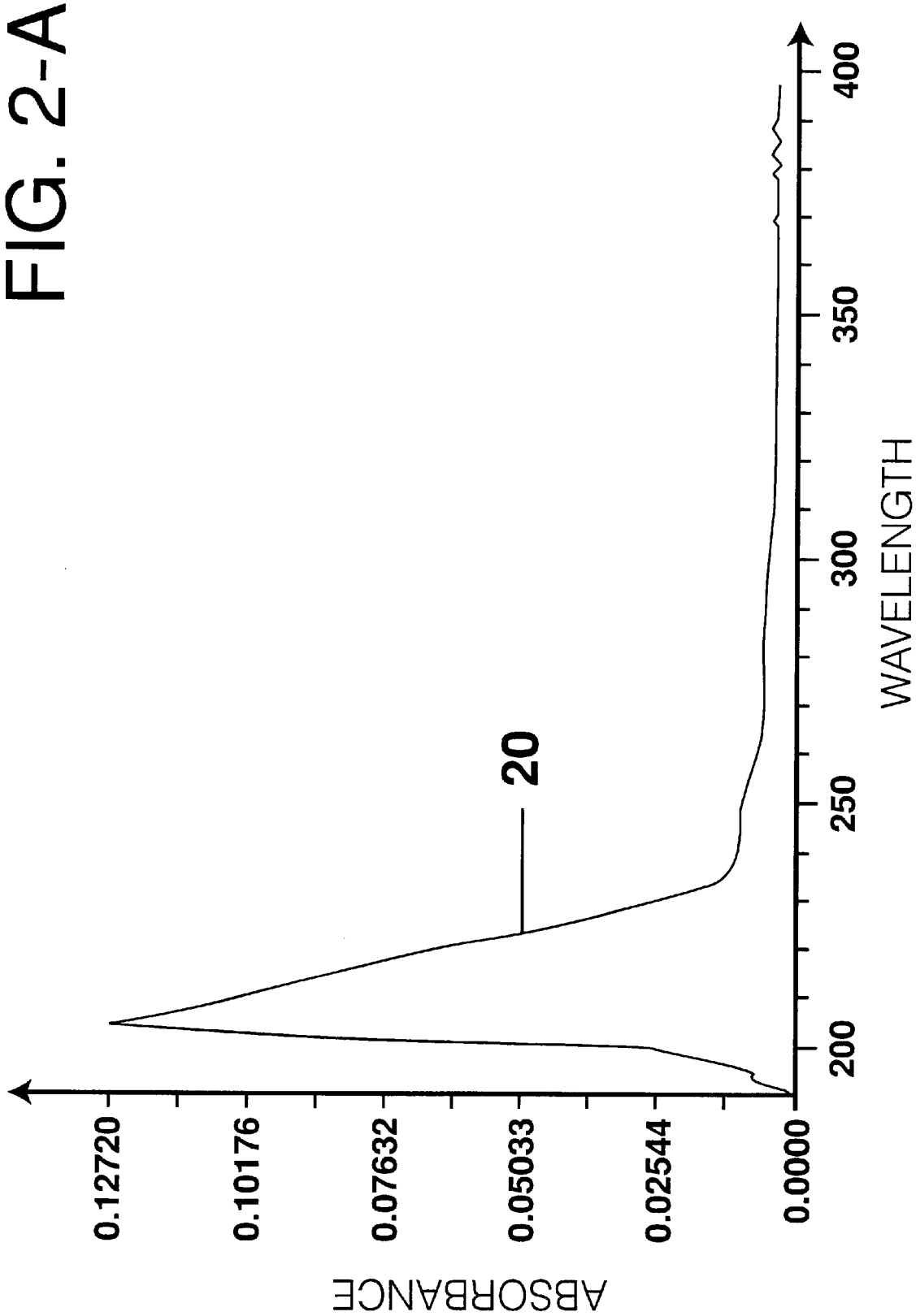

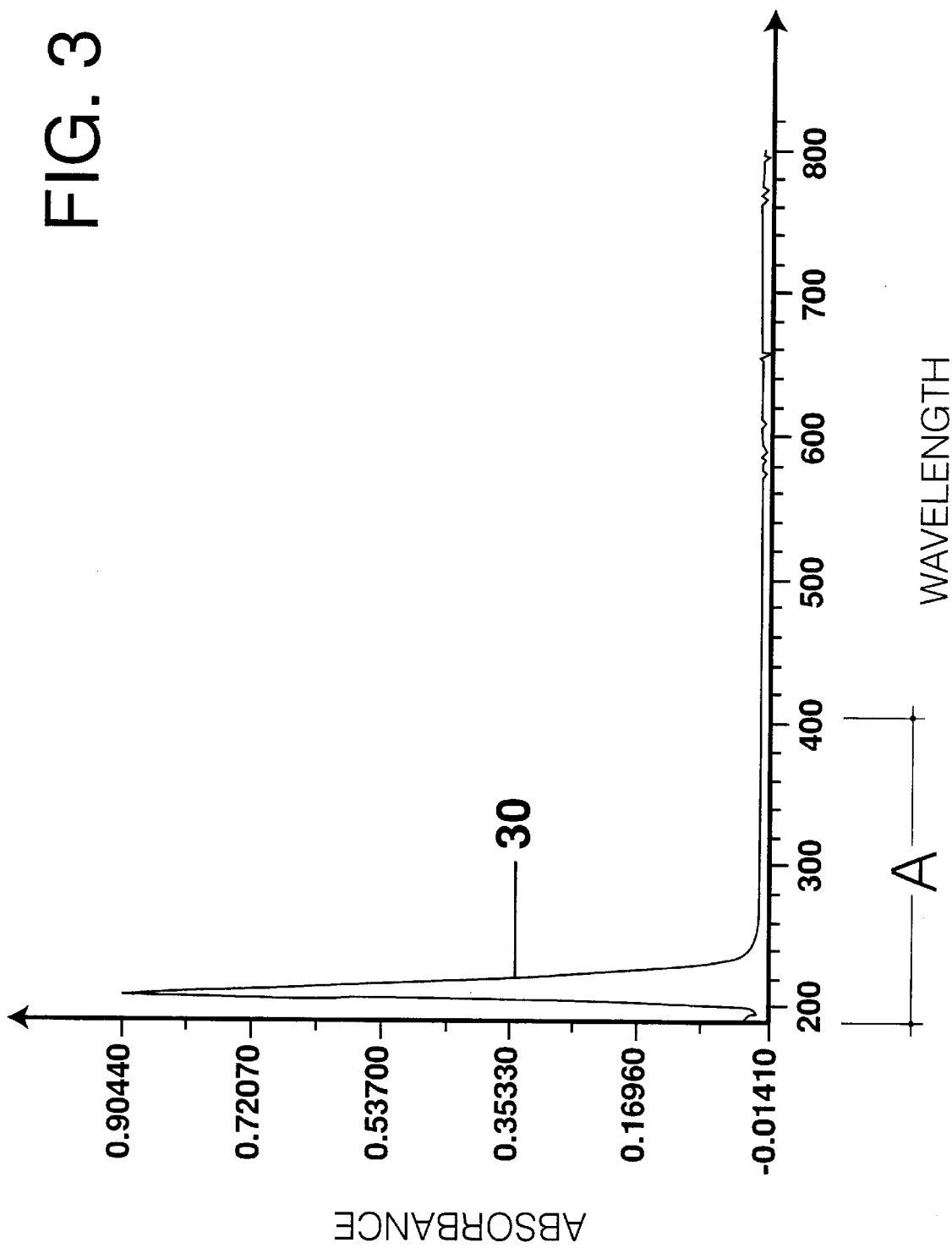

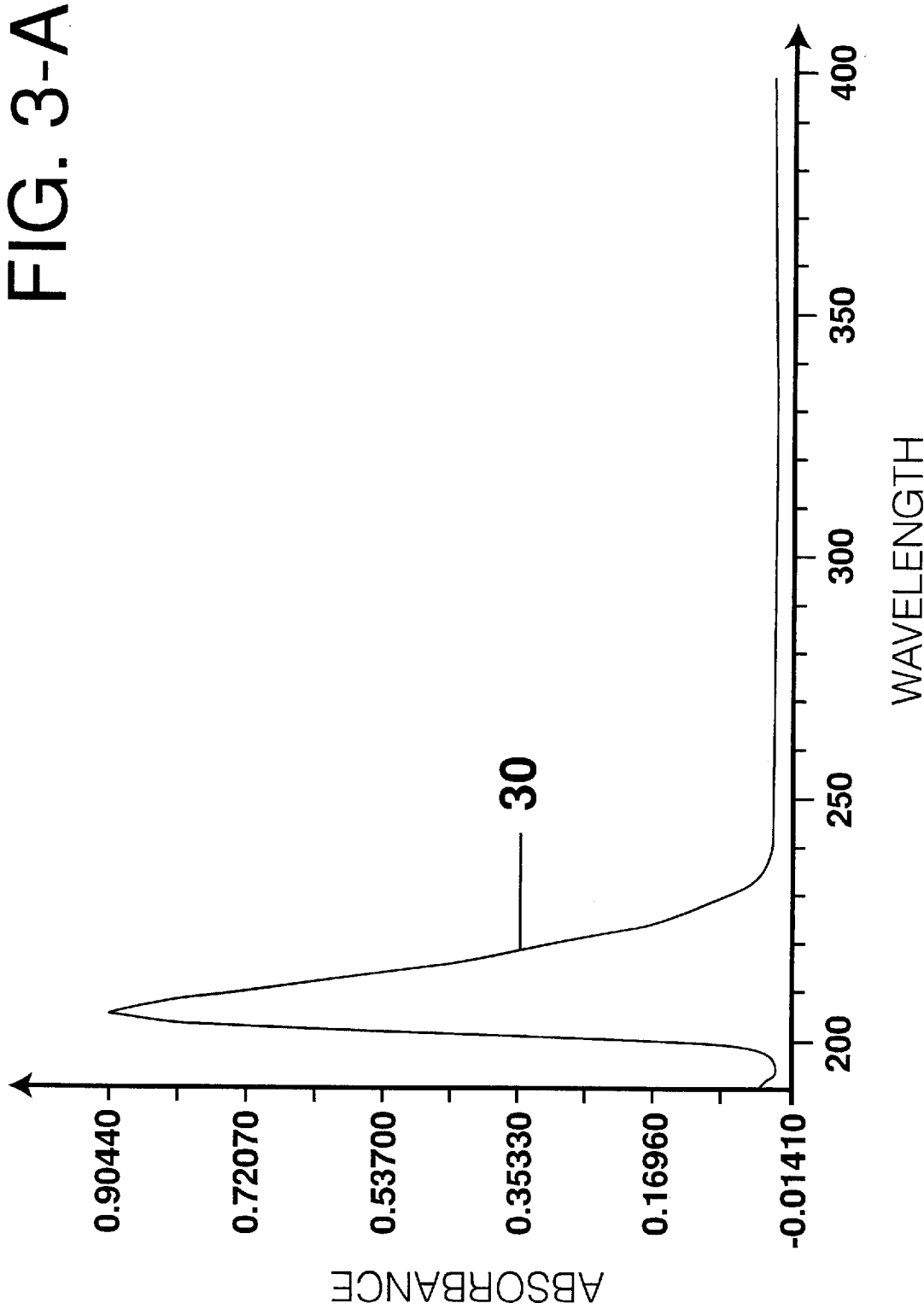
FIG. 3-A

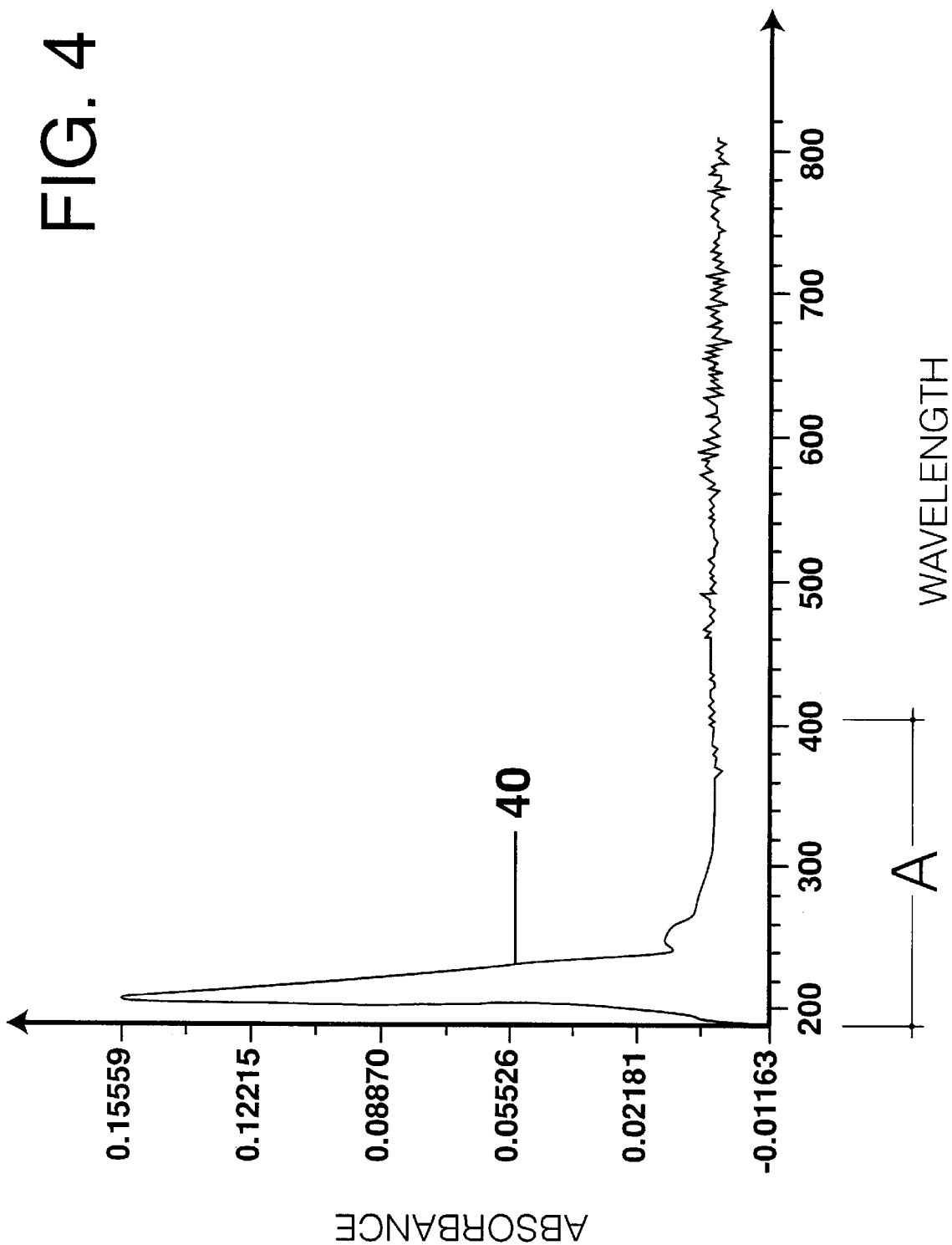

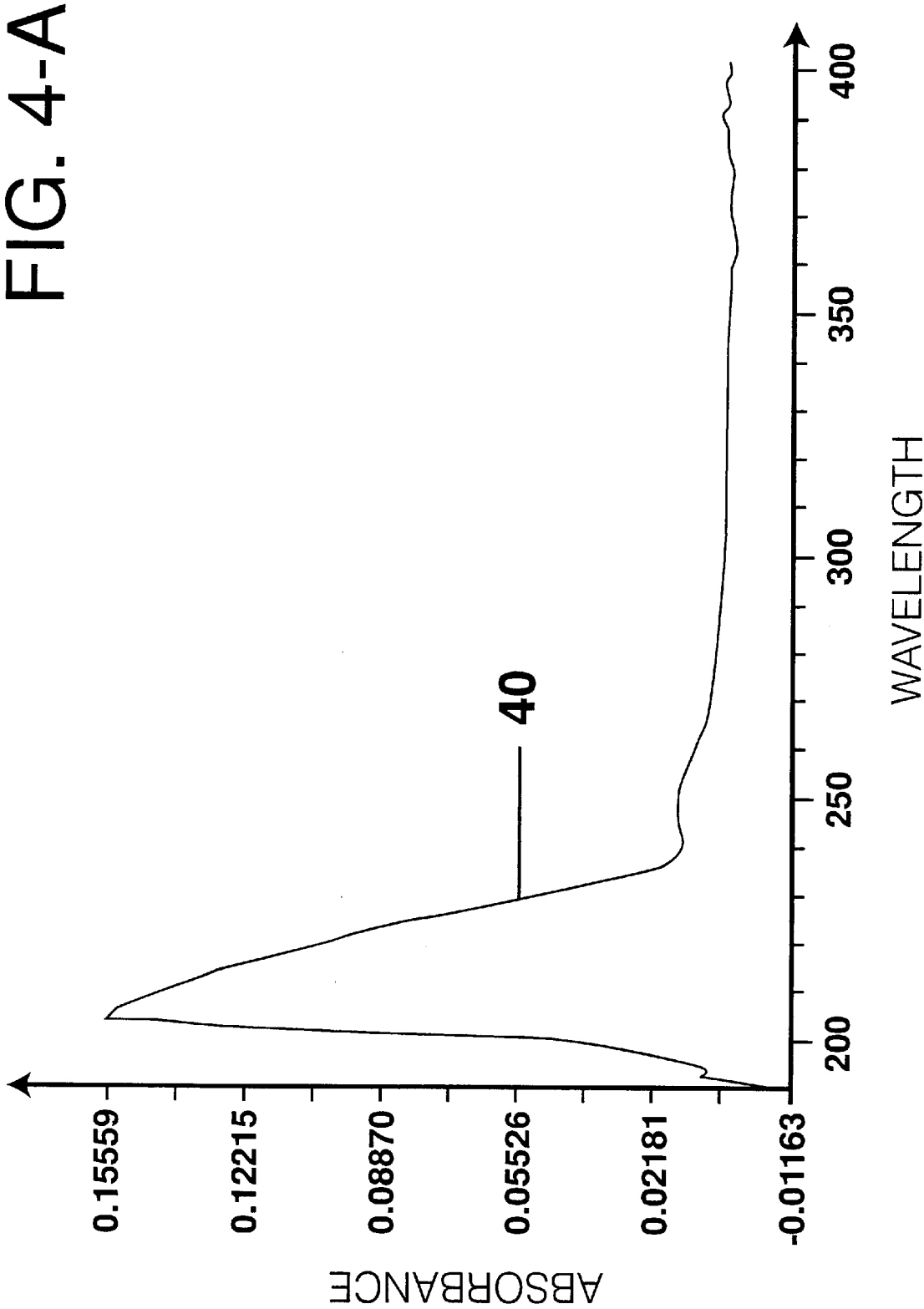
FIG. 4-A

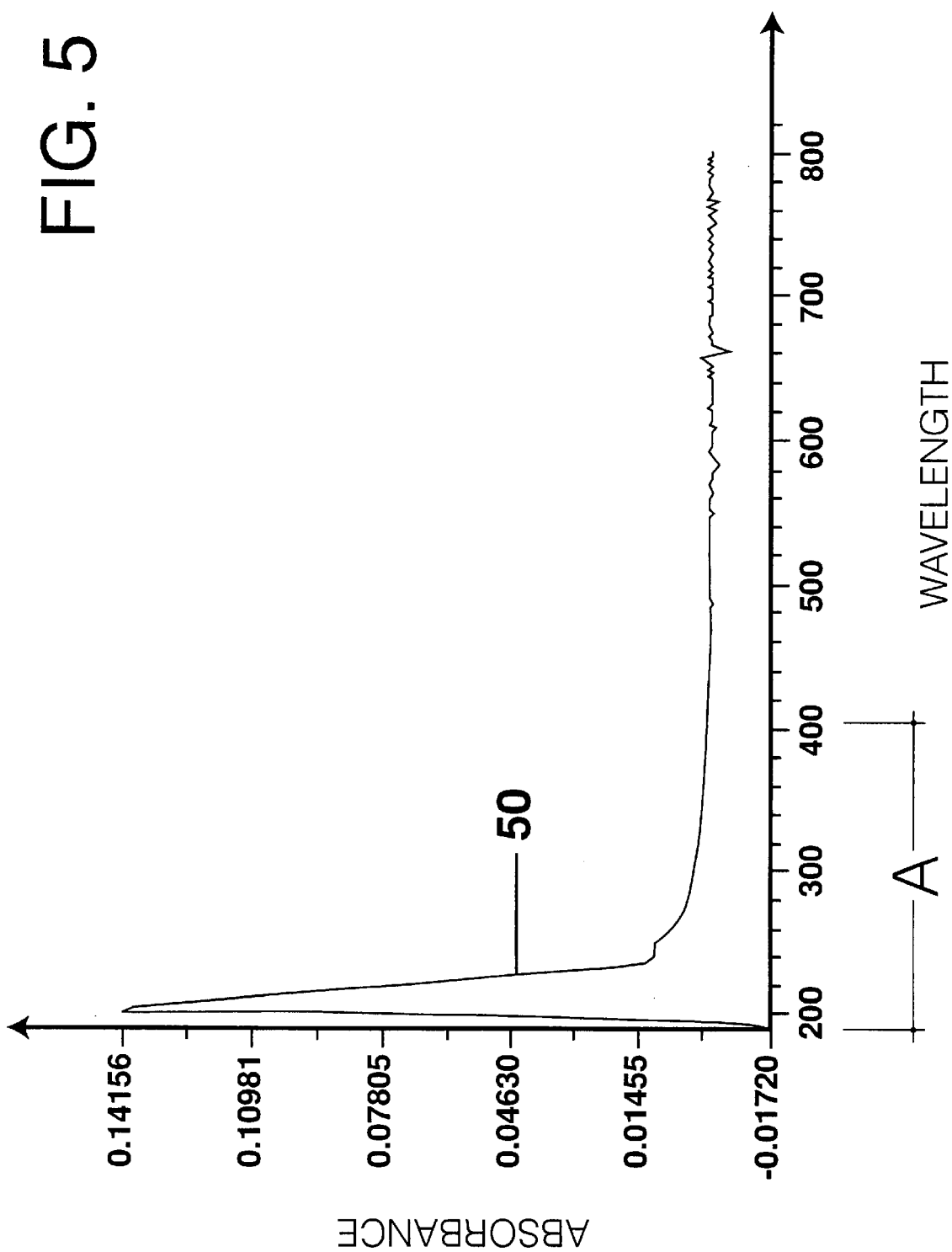

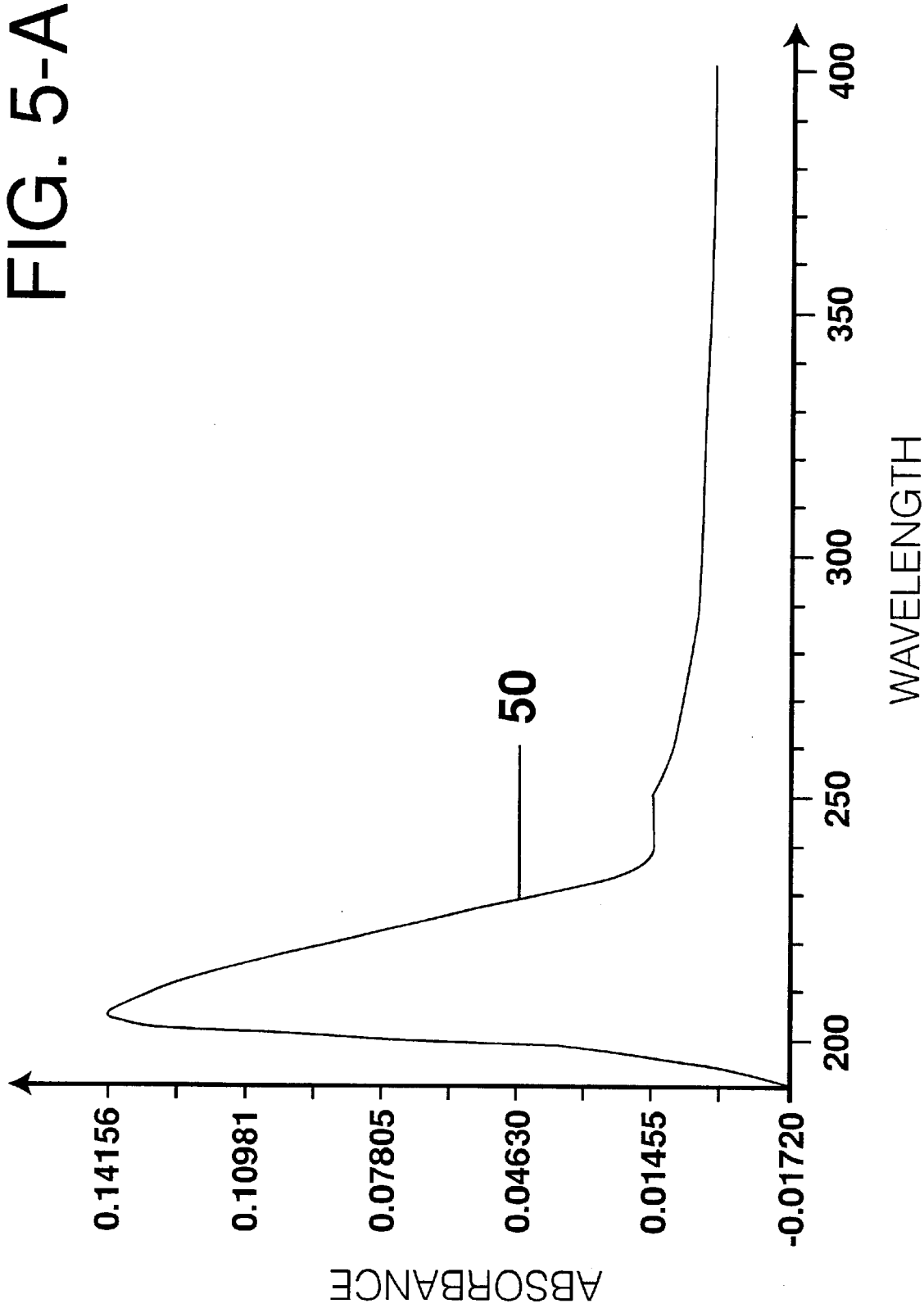
FIG. 5-A

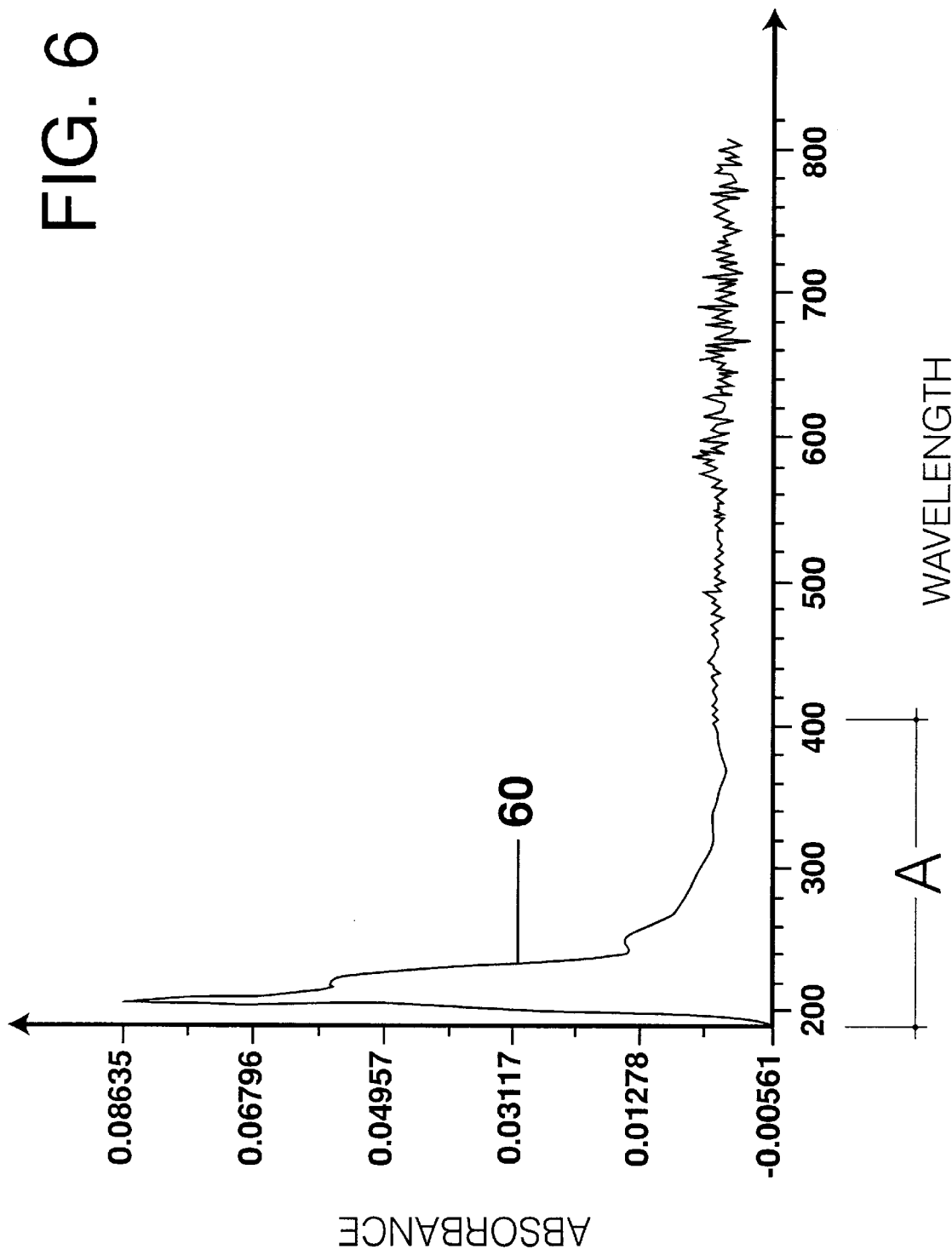

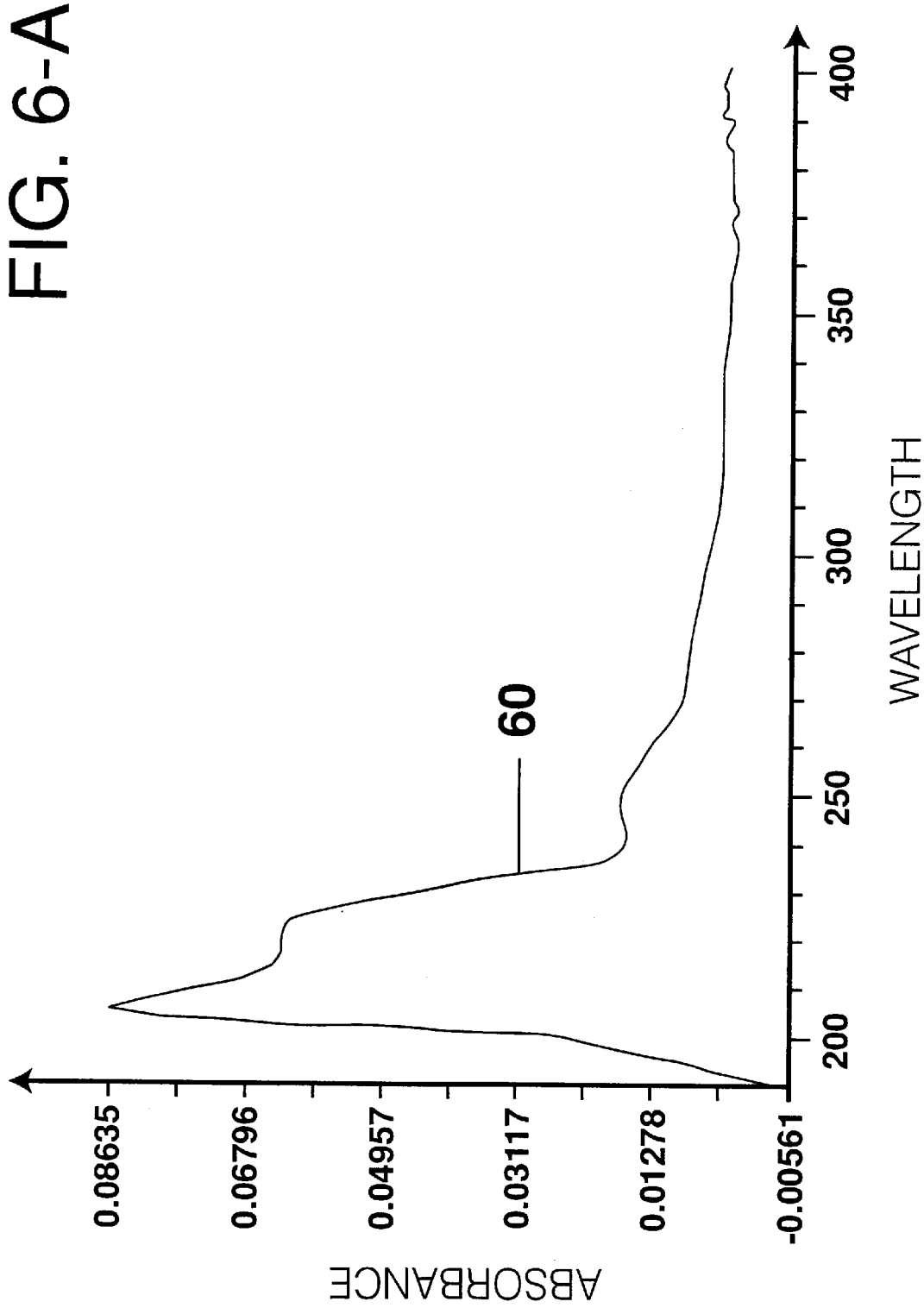
FIG. 6-A

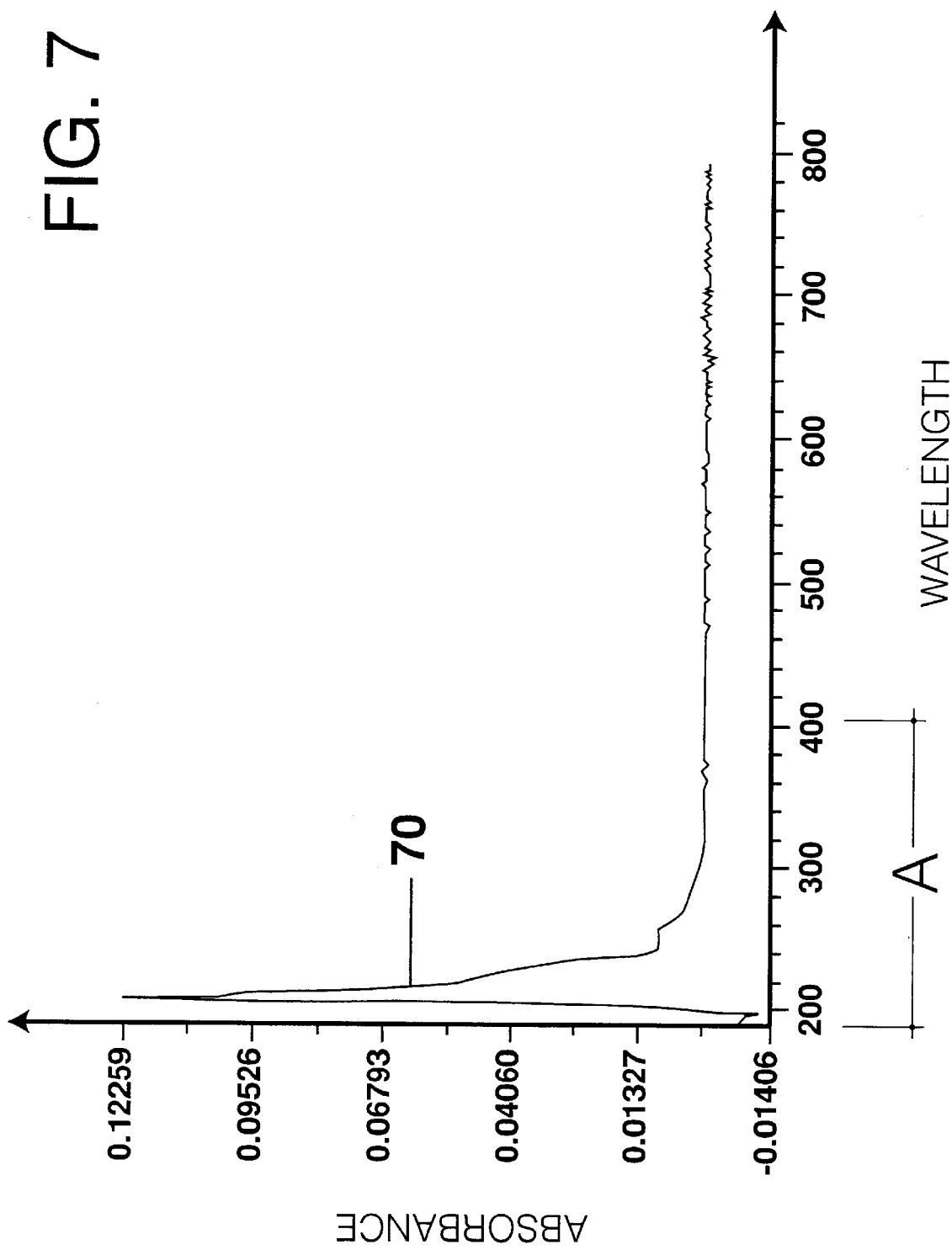

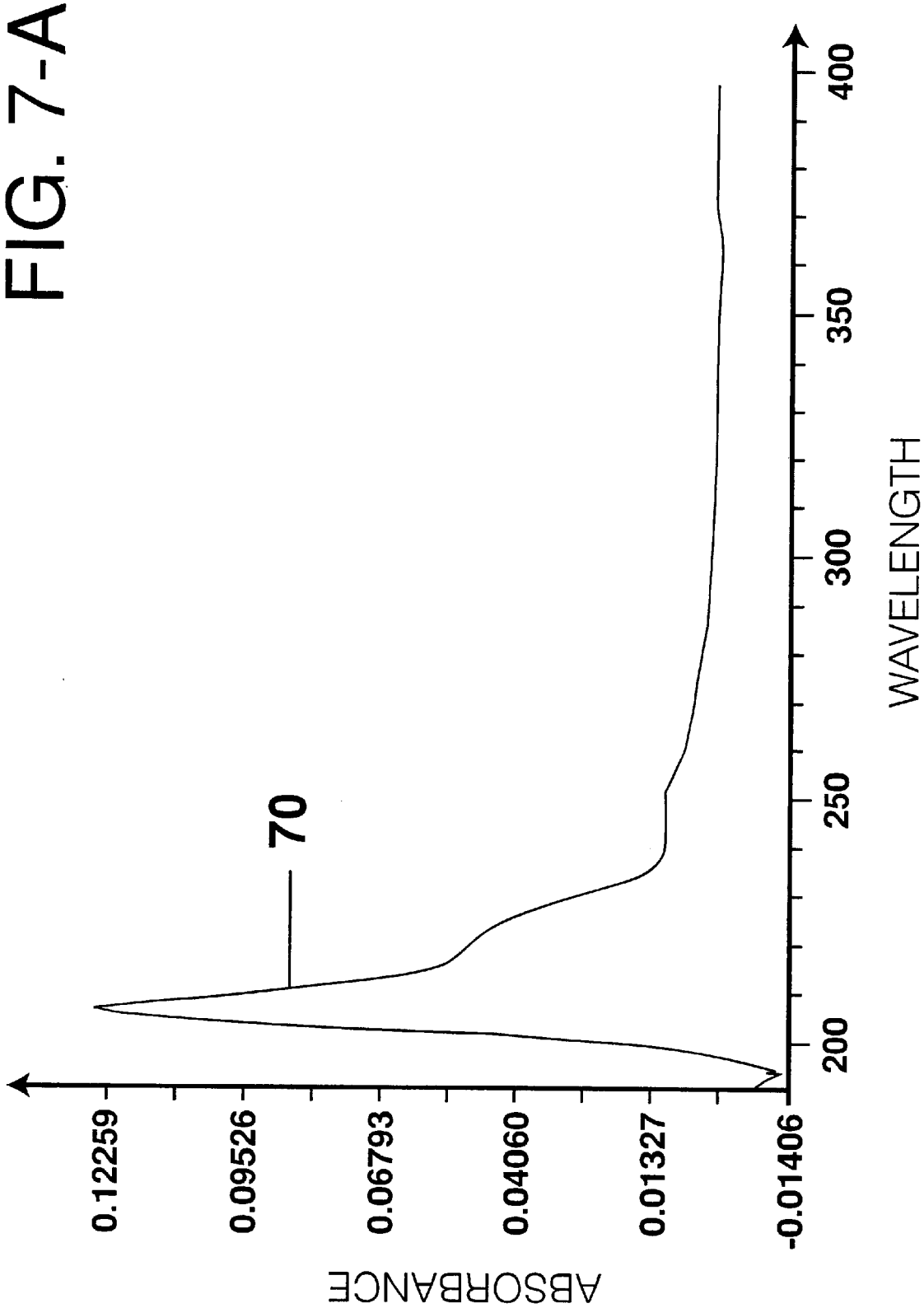

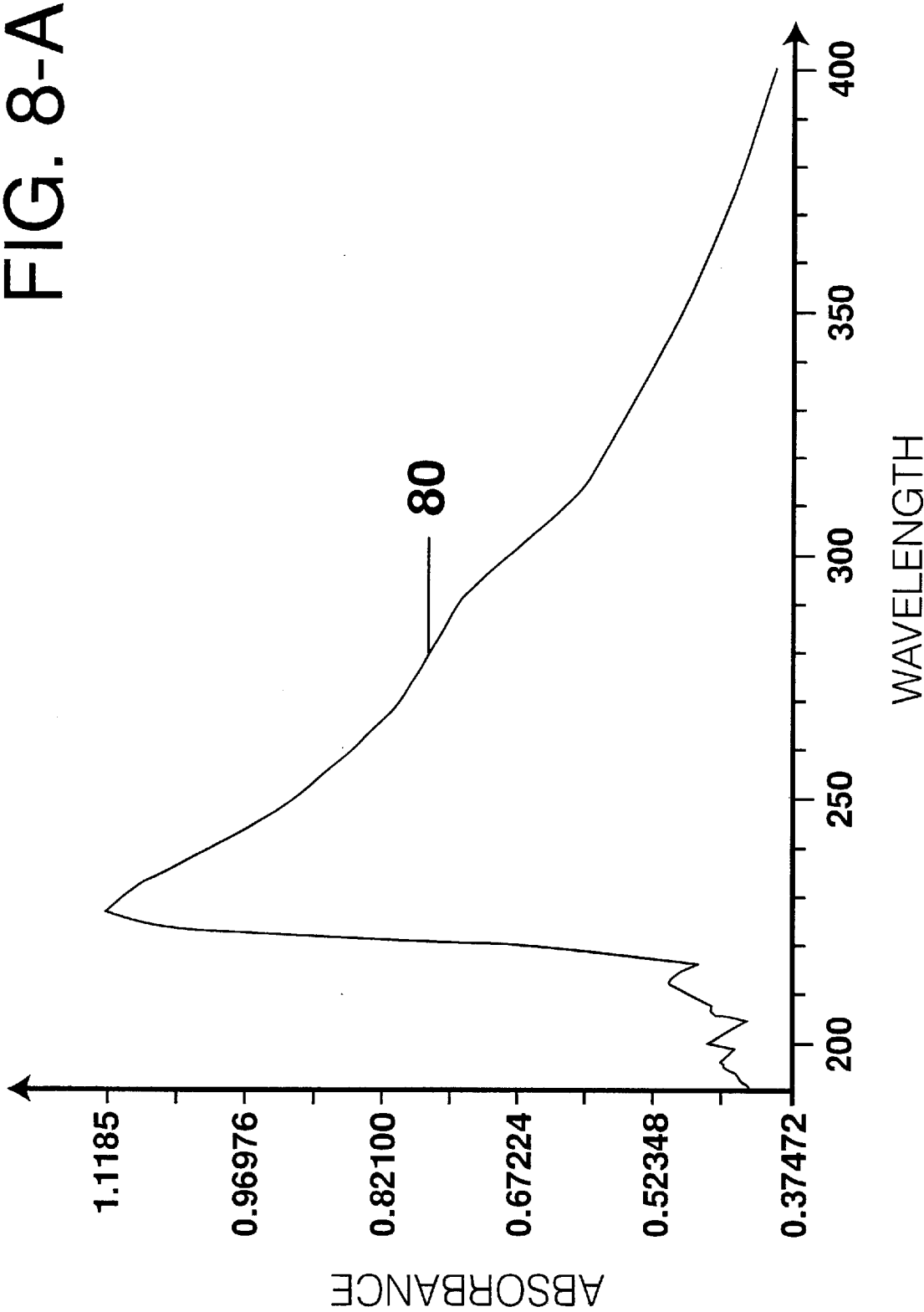

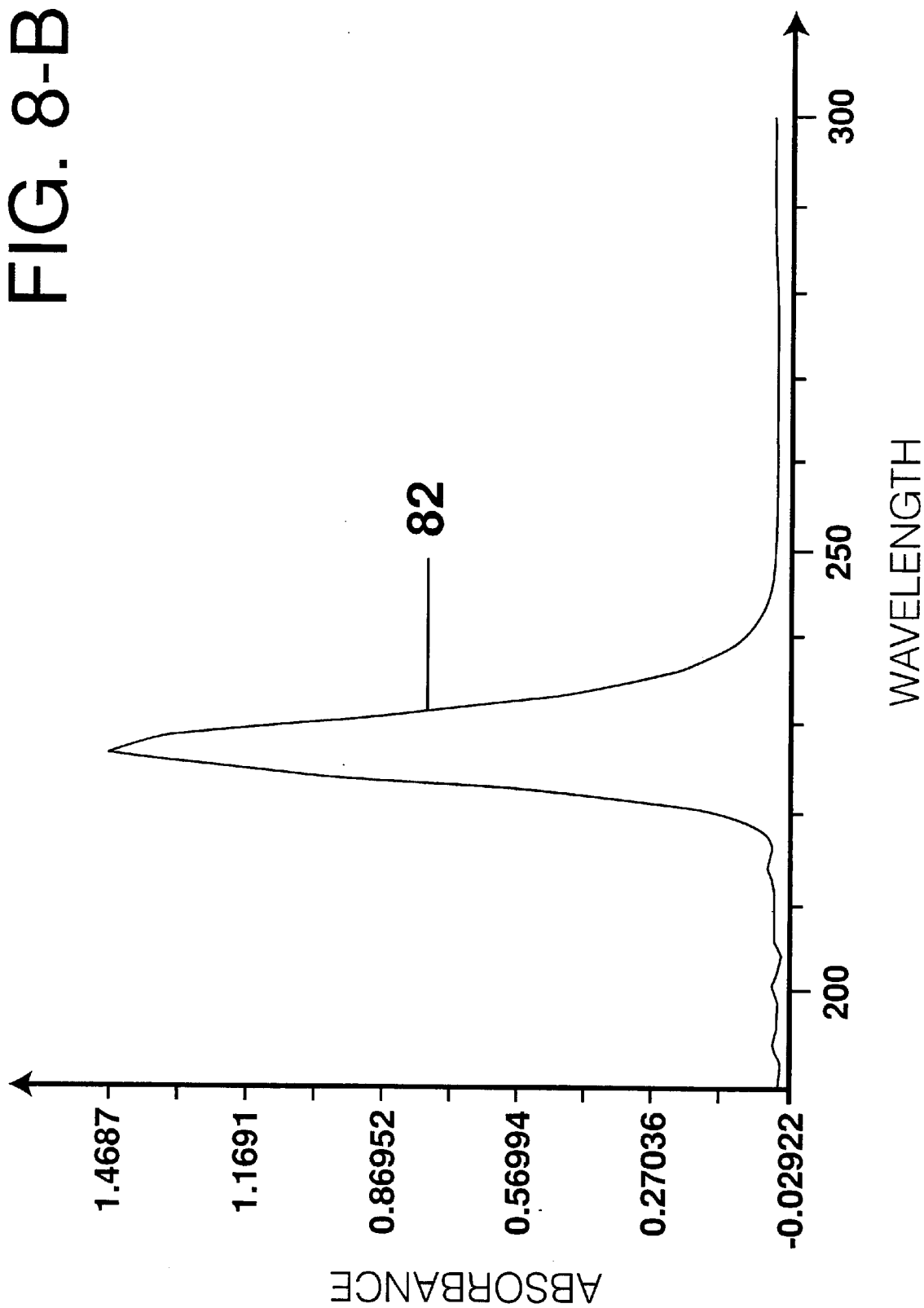
FIG. 8-B

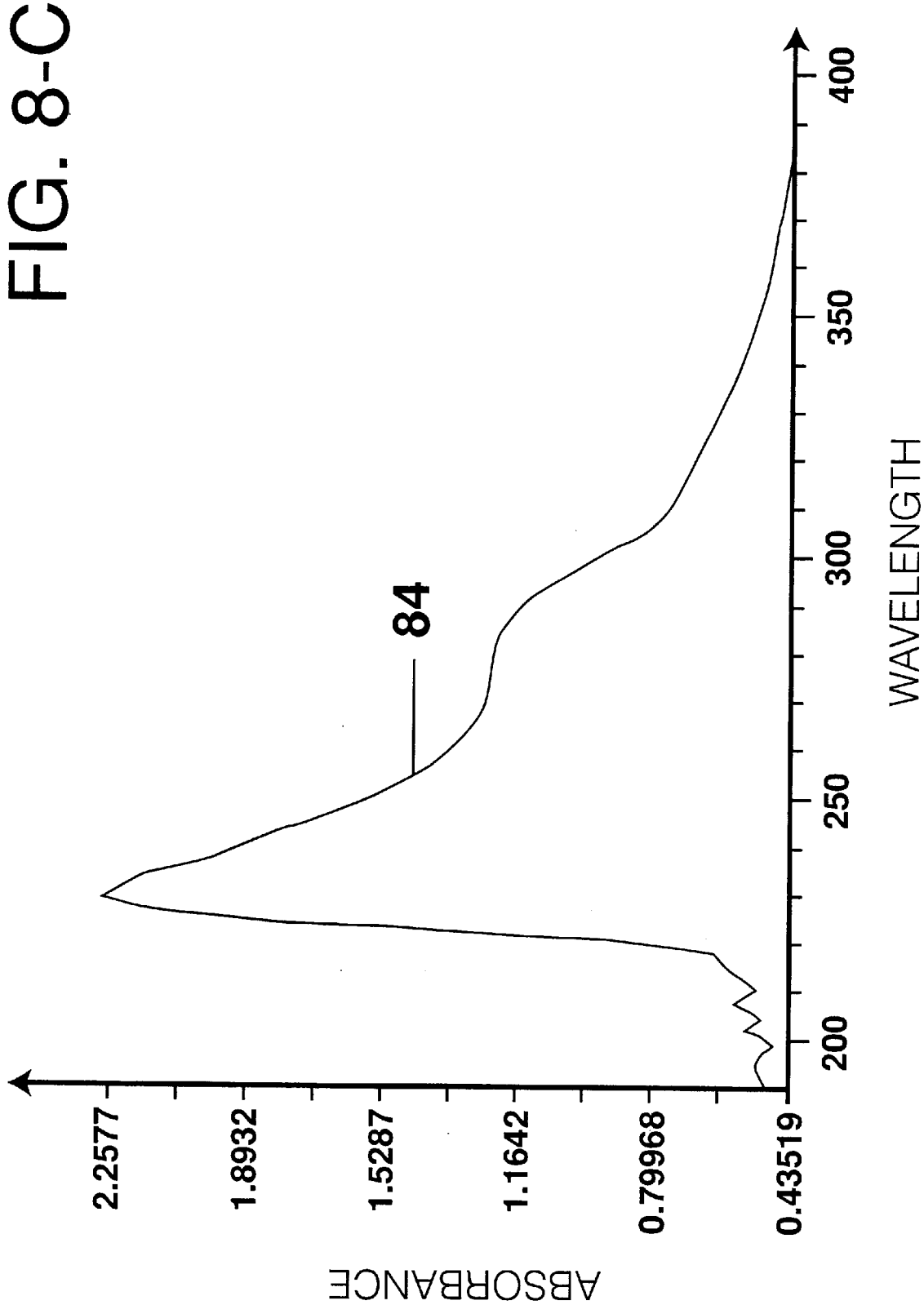
FIG. 8-C

ORAL SENSORY PERCEPTION-AFFECTING COMPOSITIONS CONTAINING DIMETHYL SULFOXIDE, COMPLEXES THEREOF AND SALTS THEREOF

BACKGROUND OF THE INVENTION

Our invention relates to oral sensory perception-affecting compositions containing dimethyl sulfoxide, complexes thereof and salts thereof, specifically comprising (i) dimethyl sulfoxide and (ii) a second compound or group of compounds:

(a) containing at least one menthyl moiety; and/or (b) containing at least one vanillyl moiety; and/or (c) containing at least one carboxamide moiety.

The term "oral sensory perception-affecting compositions" is intended to cover "coolant compositions" as well as "heat compositions."

Compositions containing compounds producing a cooling sensation, specifically hydroxy methyl or hydroxy ethyl derivatives of paramenthane are disclosed in U.S. Pat. No. 4,029,759. Such compositions are disclosed to be useful, for example, for spearmint flavor used in toothpastes, as well as other ingestible materials such as margarine and the like. Breath freshening edible compositions of menthol and a carboxamide are disclosed in U.S. Pat. No. 5,009,893. "Hot, tingling, burning, numbing" causing sensations by use of 4-(1-menthoxymethyl)-2-phenyl-1,3-dioxolane or a derivative thereof is disclosed in U.S. Pat. No. 5,545,424 issued on Aug. 13, 1996. Combinations of coolant compositions comprising a ketal and a secondary coolant which may be menthol are disclosed in PCT Application No. 93/23005 published on Nov. 25, 1993. Production of chewing gum containing controlled release acyclic carboxamides as cooling agents are disclosed in PCT Application No. 99/13870 published on Mar. 25, 1999. Chewing gum production using modified, physiological cooling agents, to wit: menthol, menthone and a carboxamide or a ketal or a diol or a succinate or mixtures of same, are disclosed in PCT Application No. 99/13734 published on Mar. 25, 1999.

However, there exists an ongoing need to provide enhancement of such "hot" sensations or such "cooling" sensations in various edible compositions, including beverages, toothpastes, throat lozenges, mouthwashes, dental floss, chewing gums, edible films such as breath freshener films and chewable pharmaceutical products, particularly wherein such "enhancement" raises the level of the "hot" or "cooling" sensation on ingestion of the edible composition, on a scale of 0–10, from about 2 up to about 10. The provision of such enhancement properties has heretofore been unknown and not implied in any prior art. Accordingly, nothing in the prior art sets forth the use of combinations of dimethyl sulfoxide with compounds containing at least one menthyl moiety, compounds containing at least one vanillyl moiety and/or compounds containing at least one carboxamide moiety in order to enhance oral sensory perception, including "hot" sensations and "cool" sensations.

Indeed, the use of dimethyl sulfoxide in foodstuffs and the presence of dimethyl sulfoxide in foodstuffs is well known. Thus, dimethyl sulfoxide is set forth in the TNO Nutrition and Food Research Institute's *Volatile Compounds in Food/ Qualitative and Quantitative Data,* Seventh Edition 1996 (Editors: L. M. Nijssen, et al.) at page 8 under CAS No. 67/68/5. Dimethyl sulfoxide is also on the GRAS list as published in *GRAS Flavoring Substances* 18, the 18th publication by the Flavor and Extract Manufacturers' Association's Expert Panel on recent progress in the consideration of the flavoring ingredients generally recognized as safe for use in food (reference: *Cooked Food Technology,* September 1998, Volume 52, No. 9 (GRAS No. 3875)) (also called "methyl sulfoxide," "DMSO" and "methyl sulfinyl methane." Nothing in the prior art discloses the effect of dimethyl sulfoxide on other sensory affecting agents, particularly oral sensory perception-affecting compositions such as coolant compositions or "hot, burning, bitter" compositions.

THE INVENTION

Our invention is directed to oral sensory perception-affecting compositions containing dimethyl sulfoxide, complexes thereof and salts thereof, specifically comprising:

(i) dimethyl sulfoxide having the structure:

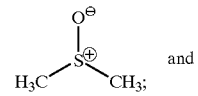

and (ii) a second compound or group of compounds:

(a) containing at least one menthyl moiety; and/or (b) containing at least one vanillyl moiety; and/or (c) containing at least one carboxamide moiety, wherein the weight ratio of "second compound(s)":dimethyl sulfoxide, is in the range of from about 1,000:1 down to about 3:1 and food grade acceptable salts thereof.

Our invention also covers oral sensory perception-affecting compositions (e.g., "coolants")-imparting consumable articles (e.g., beverages, toothpastes, throat lozenges, mouthwashes, dental floss, chewing gums, edible films and chewable pharmaceutical products). The sensory-affecting consumable articles having intensified and substantive sensory-affecting properties such as oral cooling properties and oral heating properties comprise (i) an ultimate product base and intimately admixed therewith (ii) a composition comprising (a) dimethyl sulfoxide and (b) a second compound or mixture of compounds selecting from the group consisting of compounds:

(a) containing at least one menthyl moiety; and/or (b) containing at least one vanillyl moiety; and/or (c) containing at least one carboxamide moiety wherein the weight ratio of second compound or group of compounds:dimethyl sulfoxide, is in the range of from about 1,000:1 down to about 3:10 and food grade acceptable salts thereof, wherein the concentration of dimethyl sulfoxide based on the weight of ultimate product is from about 0.05 up to about 200 parts per million (ppm) and the concentration of second compound or group of compounds or mixture of compounds is from about 2 ppm up to about 10,000 ppm on a mixed basis.

Examples of the "second compound" to be admixed with the dimethyl sulfoxide forming the mixtures of our invention are as follows:

menthol having the structure:

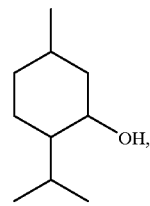

WS 23® (registered trademark of the Warner Lambert Company) having the structure:

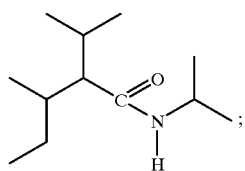

menthyl succinate having the structure:

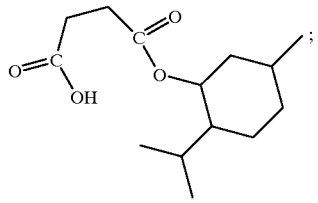

the monomenthyl ether of glycerin having the structure:

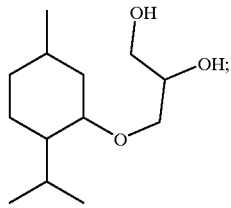

WS 3® (registered trademark of the Warner Lambert Company) having the structure:

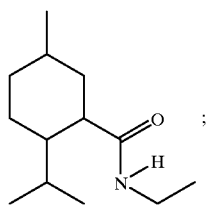

the compound having the structure:

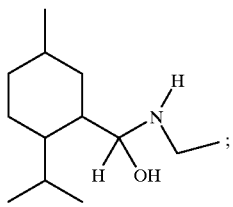

the compound having the structure:

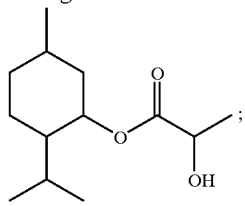

the compound having the structure:

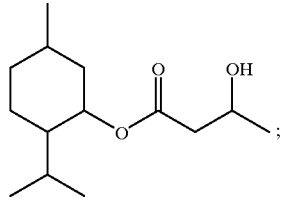

the compound having the structure:

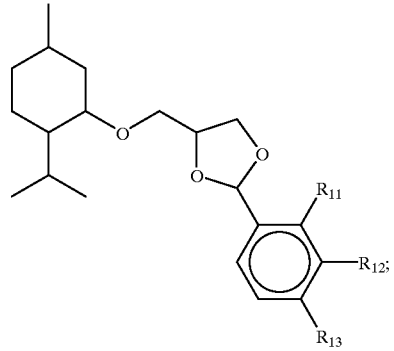

the compound having the structure:

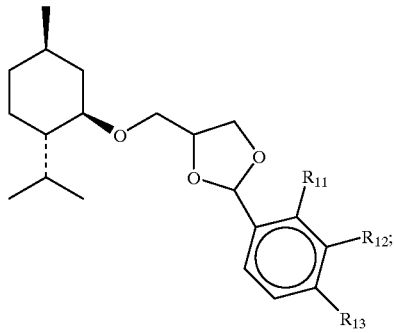

the compound having the structure:

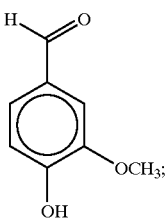

the compound having the structure:

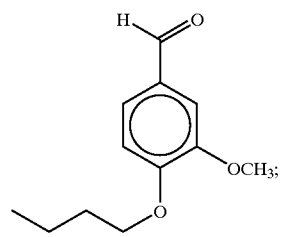

the compound having the structure:

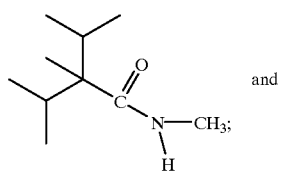

and the compound having the structure:

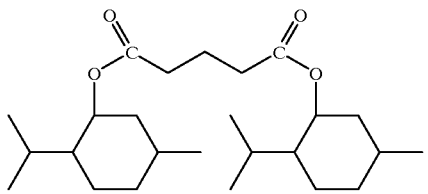

When dimethyl sulfoxide having the structure:

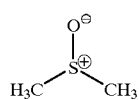

is admixed with such "second compound(s)," the resulting mixture as stated, supra, has a highly intensified oral sensory perception effect, for example, a "highly intensified cooling effect" or a "highly intensified hot, burning effect." Such effects are highly desirable in the use of certain oral care products such as mouthwashes, toothpastes and the like as set forth, supra. Thus, the following Table I sets forth a comparison of a "control" which is a "second compound" taken alone vs. the mixture of dimethyl sulfoxide with the said "second compound":

TABLE I

| "Second Compounds" | Second Compound (ppm) | Dimethyl Sulfoxide (DMSO) (ppm) | Effect of Mixture vs. Control—Comparison on a Scale 0–10 |
|---|---|---|---|
| Menthol | 5 | 0.1 | increase in perceived cooling—8 vs. 1.5 |
| Menthol | 10 | 1 | increase in perceived cooling—9 vs. 1.3 |
| Menthol | 30 | 5 | increase in perceived cooling—9.5 vs. 1.1 |
| Menthol | 100 | 10 | increase in perceived cooling—8.7 vs. 2 |
| Menthyl lactate | 30 | 0.1 | increase in perceived cooling—8.4 vs. 1.7 |
| Menthyl lactate | 30 | 100 | increase in perceived cooling—8.2 vs. 2.1 |
| Monomenthyl succinate | 100 | 0.1 | increase in perceived cooling—9.1 vs. 3.8 |
| Monomenthyl succinate | 100 | 100 | increase in perceived cooling—8.7 vs. 2.5 |
| 50-50 (weight-weight) Mixture of mono- and dimenthyl glutarates | 100 | 0.1 | increase in perceived cooling—9.6 vs. 3.3 |
| 50-50 (weight-weight) Mixture of mono- and dimenthyl glutarates | 100 | 100 | increase in perceived cooling—9.4 vs. 3.2 |
| WS 3 ®[1] | 30 | 0.1 | increase in perceived cooling—9.3 vs. 1.5 |

TABLE I-continued

| "Second Compounds" | Second Compound (ppm) | Dimethyl Sulfoxide (DMSO) (ppm) | Effect of Mixture vs. Control—Comparison on a Scale 0–10 |
|---|---|---|---|
| WS 3 ®[1] | 30 | 100 | increase in perceived cooling —9.0 vs. 1.6 |
| WS 23 ®[2] | 30 | 0.1 | increase in perceived cooling—9.6 vs. 2.4 |
| WS 23 ®[2] | 30 | 100 | increase in perceived cooling—9.2 vs. 2.2 |
| TAKOOL ®[3] | 30 | 0.1 | increase in perceived cooling—8.6 vs. 2.8 |
| TAKOOL ®[3] | 30 | 100 | increase in perceived cooling—8.2 vs. 2.6 |

Notes:

[1] WS 3 ® is a registered trademark of the Warner Lambert Company;

[2] WS 23 ® is a registered trademark of the Warner Lambert Company; and

[3] TAKOOL ® is a registered trademark of Takasago International Corporation of Tokyo, Japan and has the structure:

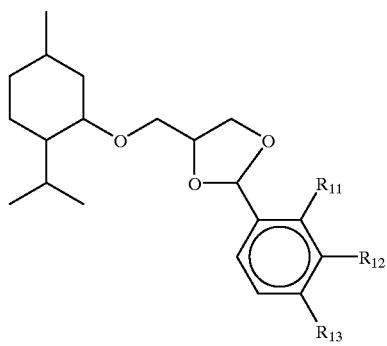

wherein $R_{11}$, $R_{12}$ and $R_{13}$ each represent hydrogen.

When the second compounds are defined according to the structures:

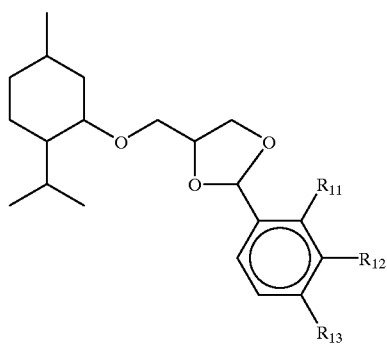

and

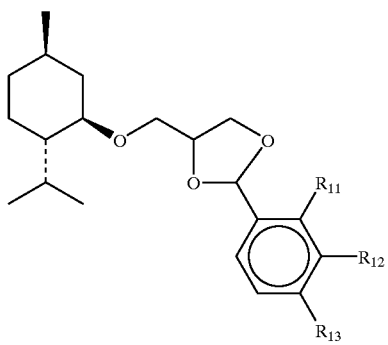

$R_{11}$, $R_{12}$ and $R_{13}$ each represents the same or different hydrogen, methyl, ethyl, n-propyl or isopropyl. Such compounds are set forth in U.S. Pat. No. 5,545,424, the specification for which is incorporated by reference herein.

The following Table II sets forth the effect in a screening base, in this case: silica toothpaste base containing 0.4% saccharin of various "second compounds" in admixture with dimethyl sulfoxide, as follows:

TABLE 11

| Screening Base | 2nd Compound (Coolant) | Use Level of 2nd Compound | ppm Dimethyl Sulfoxide (DMSO) | Observed Effect Scaled at 1–10 vs. 2nd Compound Alone |
|---|---|---|---|---|
| Silica toothpaste base with 0.4% saccharin | Menthol | 0.50% | 1 | increase in perceived cooling—8.2 vs. 1.6 |
| Silica toothpaste base with 0.4% saccharin | Mono-menthyl succinate | 100 ppm | 0.1 | increase in perceived cooling—9.0 vs. 3.5 |
| Silica toothpaste base with 0.4% saccharin | Mono-menthyl succinate | 100 ppm | 1 | increase in perceived cooling—9.2 vs. 3.7 |
| Silica toothpaste base with 0.4% saccharin | 50-50 (Weight-weight) mono- and dimenthyl glutarates | 100 ppm | 0.1 | increase in perceived cooling—9.7 vs. 3.4 |
| Silica toothpaste base with 0.4% saccharin | 50-50 (Weight-weight) mono- and dimenthyl glutarates | 100 ppm | 1 | increase in perceived cooling—9.6 vs. 3.3 |
| Silica toothpaste base with 0.4% saccharin | WS 3 ® | 30 ppm | 0.1 | increase in perceived cooling—9.1 vs. 1.7 |
| Silica toothpaste base with 0.4% saccharin | WS 3 ® | 30 ppm | 1 | increase in perceived cooling—9.0 vs. 1.6 |
| Silica toothpaste base with 0.4% saccharin | WS 23 ® | 30 ppm | 0.1 | increase in perceived cooling 9.8 vs. 2.4 |
| Silica toothpaste base with 0.4% saccharin | WS 23 ® | 30 ppm | 1 | increase in perceived cooling 9.9 vs. 2.6 |

More specifically, our invention includes coolant compositions having intensified and substantive cooling properties, as well as heat sensation-imparting compositions having intensified and substantive heat-imparting properties, consisting essentially of a product produced by the step of admixing dimethyl sulfoxide having the structure:

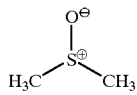

with at least one coolant or heat sensation-imparting compound having a formula selected from the group consisting of:

$$X{-}A{-}H;\ X{-}A{-}B_1;\ \text{and}\ [X{-}A^\ominus]_M [B_2^{+N}]$$

wherein the weight ratio of "coolant" or "heating" compound, dimethyl sulfoxide, is from 1,000:1 up to 3:10 and wherein X represents menthyl having the structure:

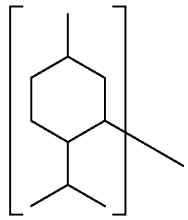

or vanillyl having the structure:

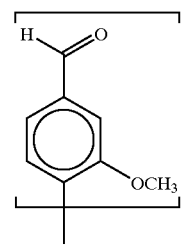

or a moiety having the structure:

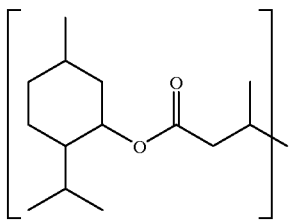

a moiety having the structure:

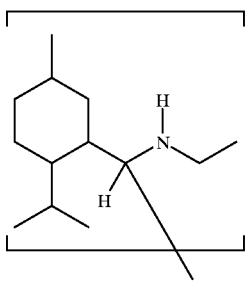

or menthoxy maleyl, succinyl, glutaryl or the like having the structure:

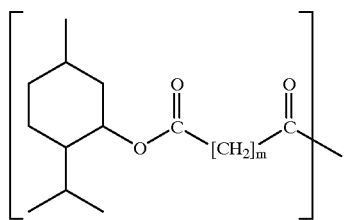

wherein m is an integer of from 1 up to 4; or n-butyl having the structure:

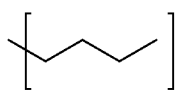

or 2,3,4-trimethyl-3-pentyl having the structure:

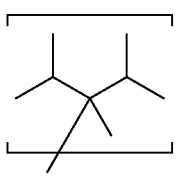

or 2,4-dimethyl-3-hexyl having the structure:

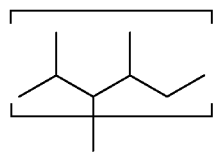

or menthoxy lactyl having the structure:

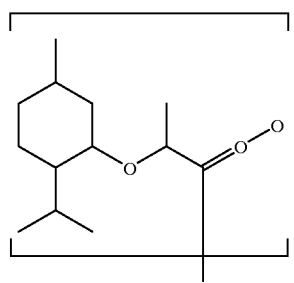

wherein A represents a divalent ether or alcohol linkage having the structure: $-[O]-$ or a divalent carbonyl linkage having the structure:

wherein $B_1$ represents one of the moieties:

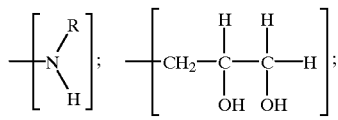

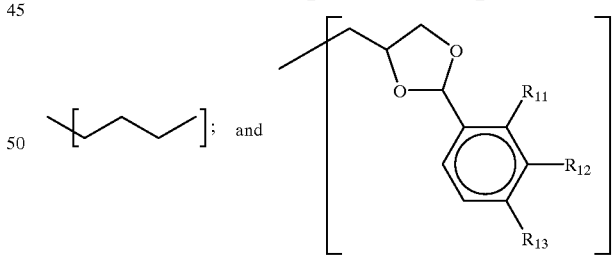

wherein $R_{11}$, $R_{12}$ and $R_{13}$ are each the same or different and each represents hydrogen and $C_1$–$C_3$ lower alkyl, that is, methyl, ethyl, n-propyl or i-propyl; and wherein $B_2$ represents one of the cations:

$[NH_4^+]$; $[Ca^{++}]$; $[Na^+]$; $[Mg^{++}]$; and/or $[K^+]$ and wherein N represents an integer of 1 or 2.

Examples of the compounds represented by the structure: X—A—H are as follows:

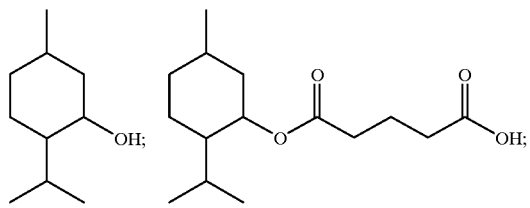

Another example of a compound represented by the structure: X—A—H is the compound having the structure:

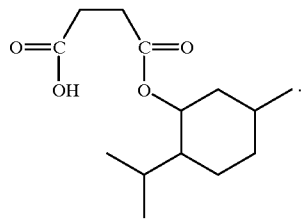

Examples of compounds represented by the structure: X—A—B₁ are as follows:

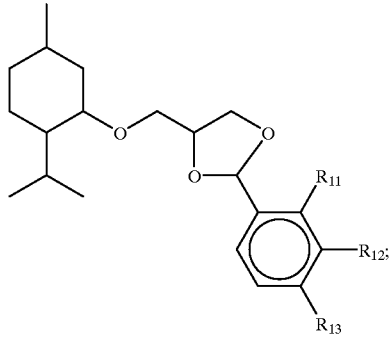

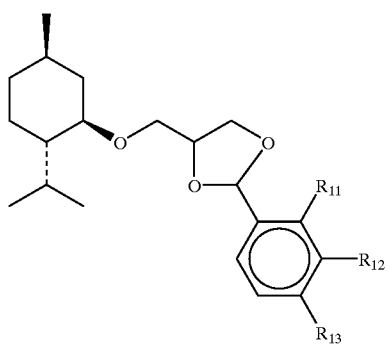

(wherein $R_{11}$, $R_{12}$ and $R_{13}$ are the same or different and each represents hydrogen or $C_1$–$C_3$ lower alkyl);

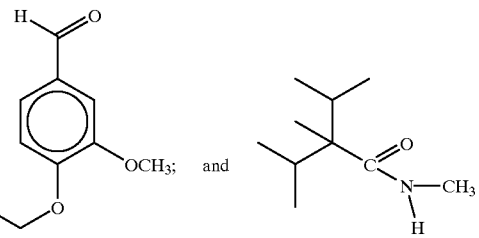

Examples of compounds represented by the structure: $[X—A^{\ominus}]_N[B_2^{+N}]$ are as follows:

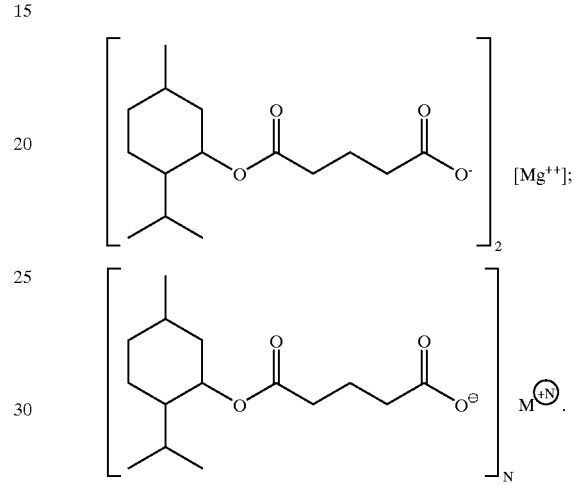

(wherein N is 1 or 2 and wherein M represents one of the cations:

$[NH_4^+]$; $[Ca^{++}]$; $[Na^+]$; $[Mg^{++}]$; and/or $[K^+]$.

When the dimethyl sulfoxide is in admixture with one of the compounds represented by one of the structures:

X—A—H; X—A—B₁; and/or $[X—A^{\ominus}]_N[B_2^{+N}]$, then complexes are formed exemplified by those having the following structures:

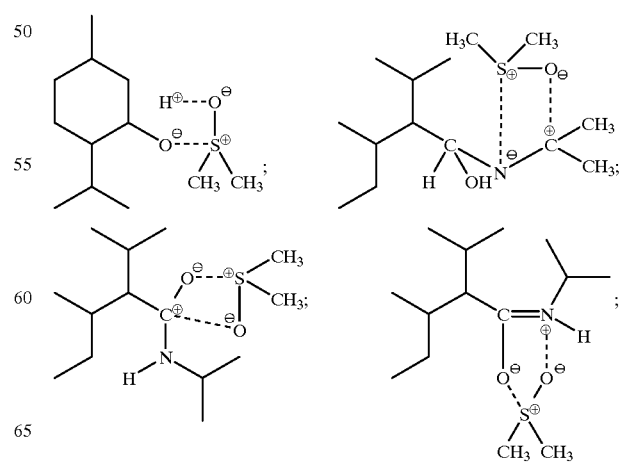

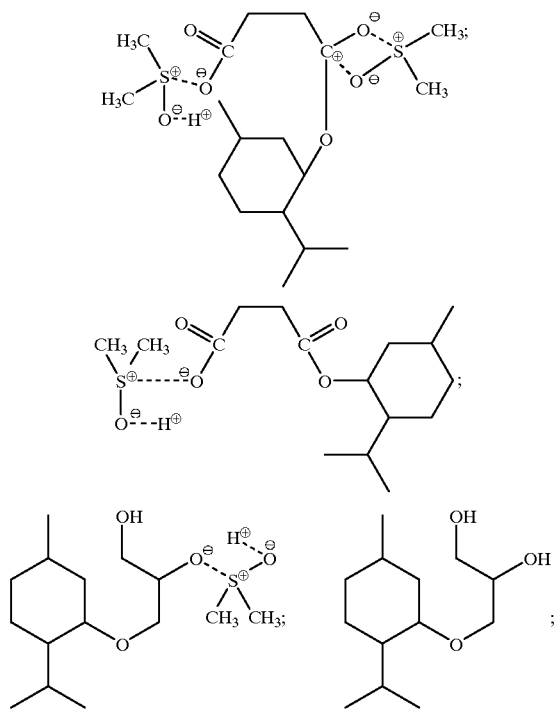
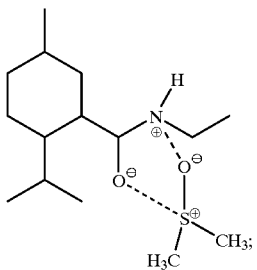
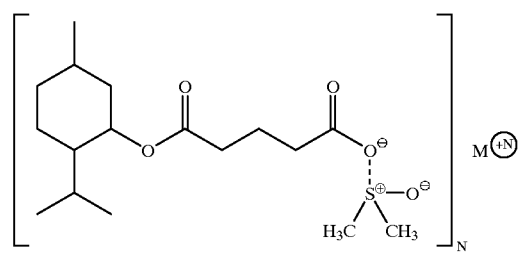
(wherein M is a cation as defined, supra; and N is an integer of 1 or 2);
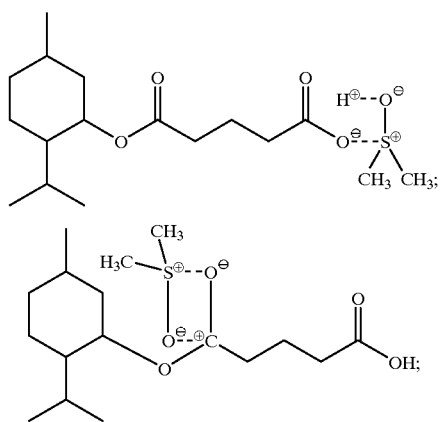
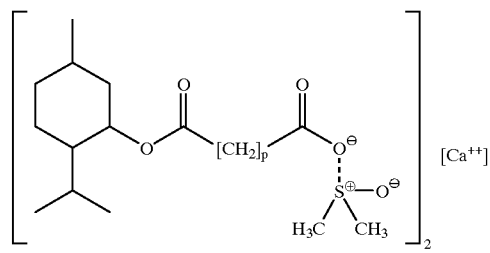
(wherein p is an integer of from 1 up to 3);
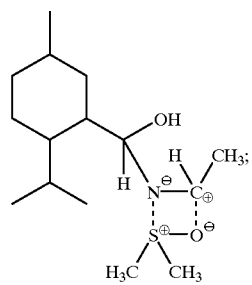
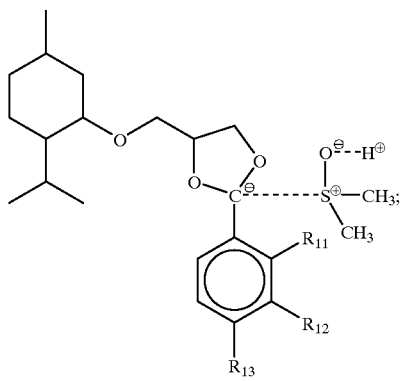
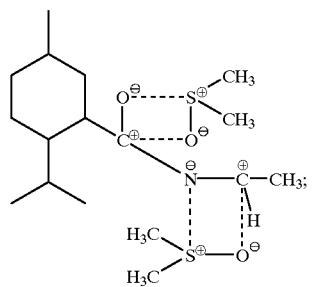
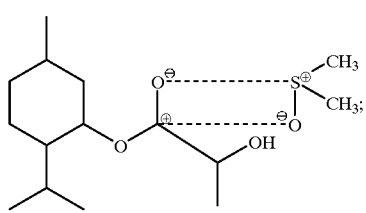

-continued

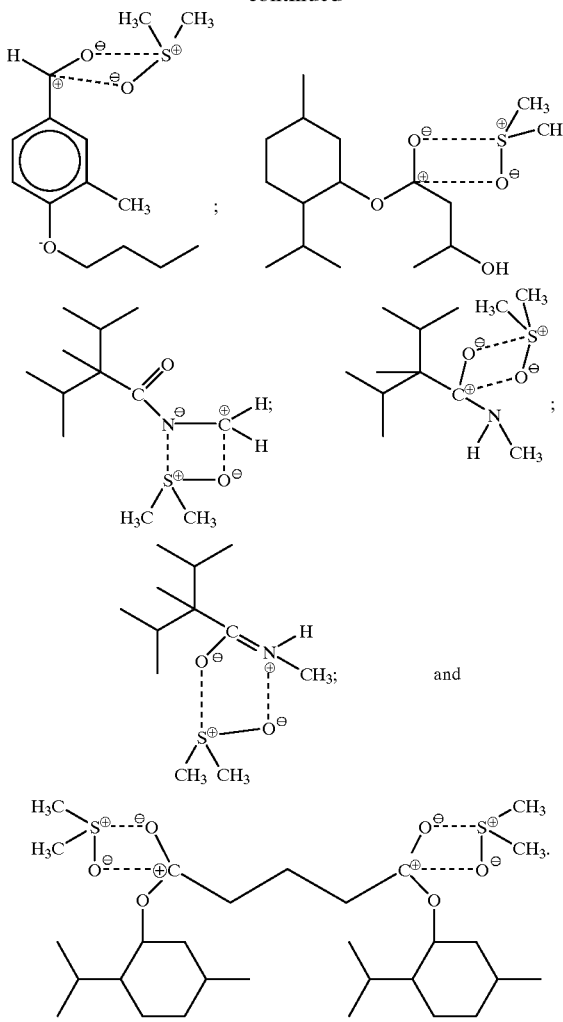

Such complexes are shown using the generic formulae:

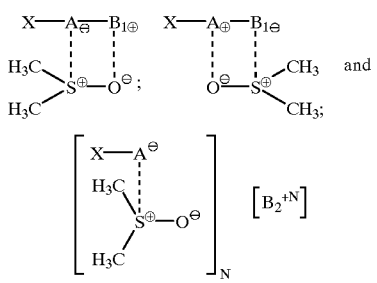

Generic reactions to form said complexes are as follows:

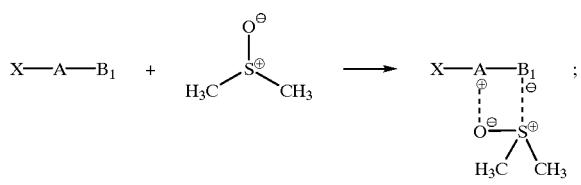

-continued

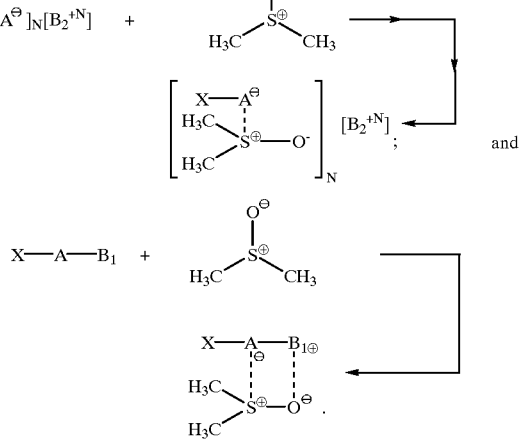

A specific reaction to form such a complex is set forth as follows:

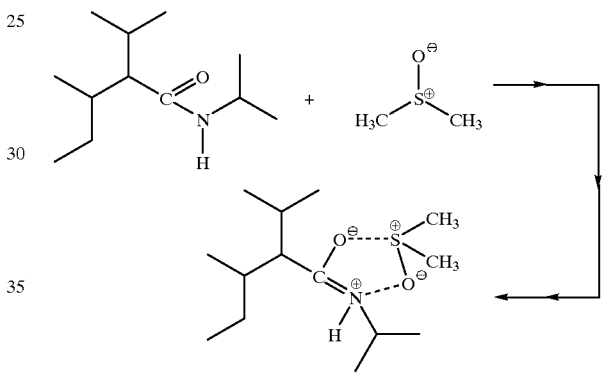

whereby the complex having the structure:

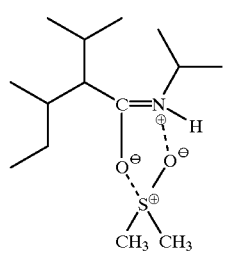

is formed.

In each of the consumable articles produced according to our invention, that is, in the beverages, toothpastes, throat lozenges, mouthwashes, dental floss, chewing gums, edible films and chewable pharmaceutical products of our invention, the concentration of dimethyl sulfoxide (on a premixed basis) based on the weight of ultimate product is from about 0.05 up to about 200 ppm. In each of the consumable articles of our invention, the concentration of second compound, that is one of the compounds having one of the structures:

X—A—H; X—A—$B_1$; and/or $[X-A^\ominus]_N[B_2^{+N}]$ on a premixed basis, based on the weight of the ultimate product, is from about 2 up to about 10,000 ppm.

An example of a breath freshener film is one produced from pullulan and modified starches containing 5% actives as produced by the Warner Lambert Company. Another example is HERB LEAF® produced by the Ha-Buri-Fu K.K. Organization of Japan under the trademark HERB LEAF® (registered trademark of the Ha-Buri-Fu K.K. Organization), specifically described in Japanese Patent No. 1843452, the specification for which is incorporated by reference herein. Other examples of products wherein the compositions of our invention are useful are as follows:

(a) toothpaste as disclosed in Examples 6–10 of U.S. Pat. No. 4,029,759 issued on Jun. 14, 1977, the specification for which is incorporated by reference herein;

(b) chewing gum compositions as set forth in Example 1 at column 10 of U.S. Pat. No. 5,009,893 issued on Apr. 23, 1991, the specification for which is incorporated by reference herein;

(c) hard candy (formed into throat lozenges) as exemplified in Example 4 of U.S. Pat. No. 5,545,424 issued on Aug. 13, 1996, the specification for which is incorporated by reference herein;

(d) mouth rinse formulations as set forth in Examples 3 and 4 of PCT Application No. WO 93/23005 published on Nov. 25, 1993, the specification for which is incorporated by reference herein;

(e) sugarless gums as set forth in Examples 30–37 in Table 7 of PCT Application No. WO 99/13870 published on Mar. 25, 1999, the specification for which is incorporated by reference herein; and (f) chewing gums as exemplified in Examples 6–10 in Table 3 of PCT Application No. WO 99/13734 published on Mar. 25, 1999, the specification for which is incorporated by reference herein.

BRIEF DESCRIPTION OF THE DRAWINGS

FIG. 1 is and ultraviolet-visible spectrum for a 1:1 mixture of dimethyl sulfide having the structure:

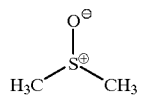

Figure 2:
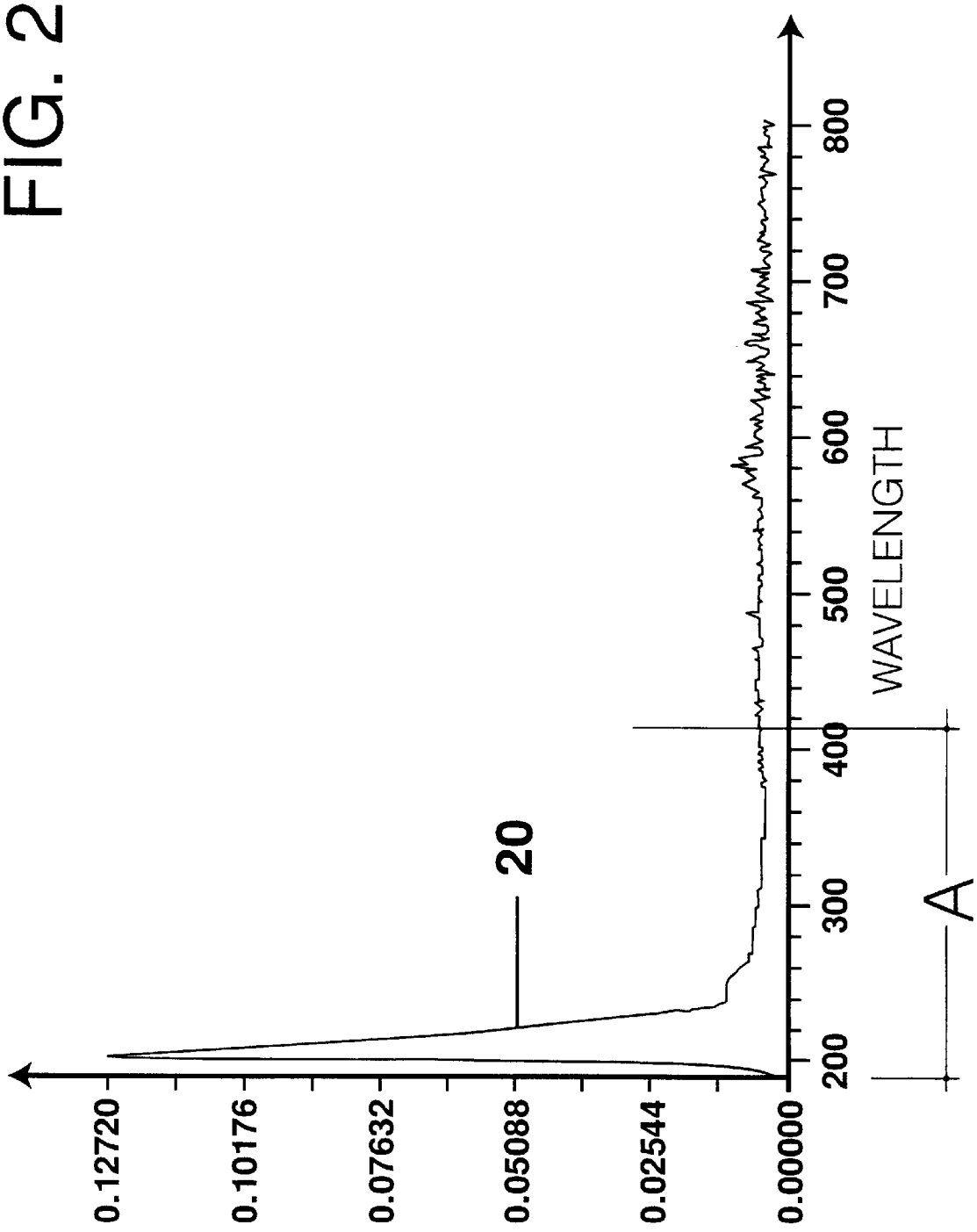

menthyl glutarates, a mixture of compounds having the structures:

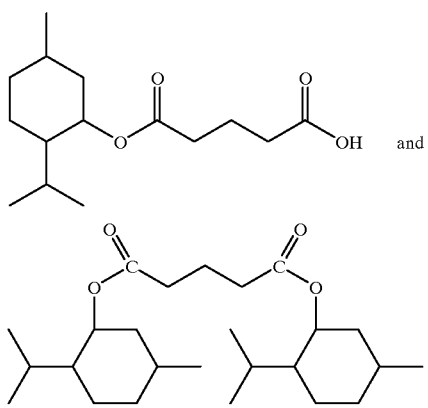

(solvent: methanol; concentration: 0.01%; wavelength range: 190–820 nm).

FIG. 1A is an ultraviolet spectrum (only) for a 1:1 mixture of dimethyl sulfoxide:menthyl glutarates (conditions: methanol solvent at a concentration of 0.01%; wavelength range: 190–400 nm).

FIG. 2 is an ultraviolet-visible spectrum for a 10:1 mixture of dimethyl sulfoxide:menthyl glutarates (conditions: methanol solvent at a 1% concentration; wavelength range: 190–820 nm).

FIG. 2A is an ultraviolet (only) spectrum for a 10:1 mixture of dimethyl sulfoxide:menthyl glutarates mixture (conditions: methanol solvent at a 1% concentration; wavelength range: 190–400 nm).

FIG. 3 is an ultraviolet-visible spectrum for a 1:1 mixture of dimethyl sulfoxide:WS 3® (registered trademark of the Warner Lambert Company) having the structure:

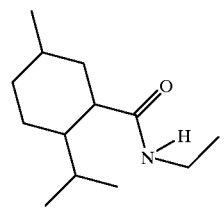

(conditions: methanol solvent at a concentration of 0.01%; wavelength range: 190–820 nm).

FIG. 3A is an ultra violet spectrum (only) for a 1:1 mixture of dimethyl sulfoxide:WS 3® (conditions: methanol solvent at a concentration of 0.01%; wavelength range: 190–400 nm).

FIG. 4 is an ultraviolet-visible spectrum (only) for a 10:1 mixture of dimethyl sulfoxide:WS 3® (conditions: methanol solvent at a concentration of 1.0%; wavelength range: 190–820 nm).

FIG. 4A is an ultraviolet spectrum (only) for a 10:1 mixture of dimethyl sulfoxide:WS 3® (conditions: methanol solvent at a concentration of 1.0%; wavelength range: 190–400 nm).

FIG. 5 is an ultraviolet-visible spectrum for dimethyl sulfoxide (only) (conditions: methanol solvent at a concentration of 1.0%; wavelength range: 190–820 nm).

FIG. 5A is an ultraviolet spectrum (only) for dimethyl sulfoxide (only) (conditions: methanol solvent at a concentration of 1.0%; wavelength range: 190–400 nm).

FIG. 6 is an ultraviolet-visible spectrum for menthyl glutarates (only) (conditions: methanol solvent at a concentration of 1.0%; wavelength range: 190–820 nm).

FIG. 6A is an ultraviolet spectrum (only) for menthyl glutarates (only) (conditions: methanol solvent at a concentration of 1.0%; wavelength range: 190–400 nm).

FIG. 7 is an ultraviolet-visible spectrum for WS 3® (only) (conditions: methanol solvent at a concentration of 1.0%; wavelength range: 190–820 nm).

FIG. 7A is an ultraviolet spectrum (only) WS 3® (only) (conditions: methanol solvent at a concentration of 1.0%; wavelength range: 190–400 nm).

FIG. 8A is an ultraviolet spectrum (only) for a 1:1 mixture of dimethyl sulfoxide:menthyl glutarates at a pH of 10 (conditions: aqueous solvent at pH of 10 at a concentration of 1.0%; wavelength range: 190–400 nm).

FIG. 8B is an ultraviolet spectrum (only) for dimethyl sulfoxide (only) at a pH of 10 (conditions: aqueous solvent at a pH of 10 at a concentration of 1.0%; wavelength range: 190–300 nm).

FIG. 8C is an ultraviolet spectrum (only) for a menthyl glutarates (only) at a pH of 10 (conditions: aqueous solvent at a pH of 10 at a concentration of 1.0%; wavelength range: 180–400 nm).

DETAILED DESCRIPTION OF THE DRAWINGS

Referring to FIG. 1, the Y axis is for absorbents and the X axis is for wavelength. The Y axis is indicated by reference numeral 14 and the X axis is indicated by reference numeral 12.

FIG. 1A is an enlargement of section "A" of FIG. 1. The peak indicated by reference numeral 10 is the peak for the absorbents in the ultraviolet range of the 1:1 mixture of dimethyl sulfoxide:menthyl glutarates. Complexes formed as a result of the interaction of the dimethyl sulfoxide with menthyl glutarates have the following structures:

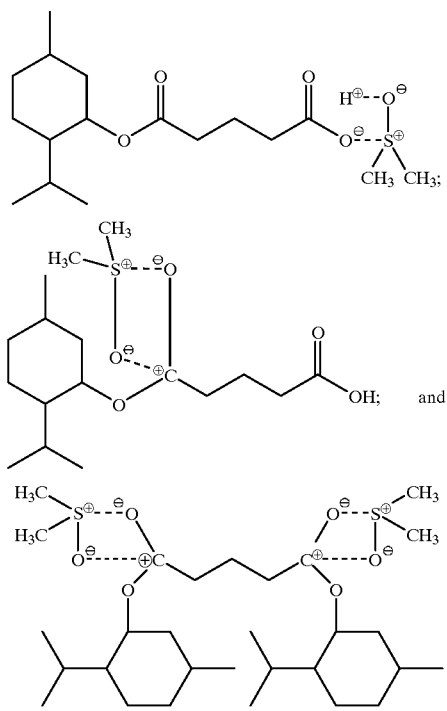

In FIGS. 2 and 2A (with FIG. 2A being an enlargement of section "A" of FIG. 2), the peak indicated by reference numeral 20 is the peak for the ultraviolet absorbtivity of the 10:1 dimethyl sulfoxide:mentyl glutarates mixture.

In FIGS. 3 and 3A (with FIG. 3A being an enlargement of section "A" of FIG. 3), the peak indicated by reference numeral 30 is the peak for the 1:1 mixture of dimethyl sulfoxide:WS 3®. The complexes formed as a result of the interaction of dimethyl sulfoxide with WS 3® are as follows:

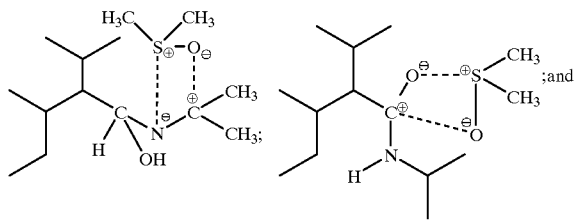

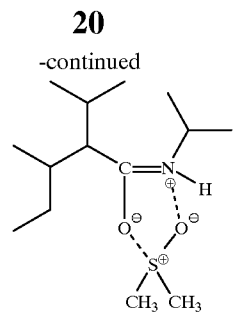

In FIGS. 4 and 4A, the peak indicated by reference numeral 40 is the peak for the ultraviolet absorbtivity of the resulting material produced by admixing dimethyl sulfoxide with WS 3® in a weight ratio of 10:1. FIG. 4A is an enlargement of section "A" of FIG. 4.

In FIGS. 5 and 5A, the peak indicated by reference numeral 50 is the peak for the ultraviolet absorbtivity of dimethyl sulfoxide alone. FIG. 5A is an enlargement of section "A" of FIG. 5.

In FIGS. 6 and 6A, the peak indicated by reference numeral 60 is the peak for the ultraviolet absorbtivity of menthyl glutarates. FIG. 6A is an enlargement of section "A" of FIG. 6.

In FIGS. 7 and 7A, the peak indicated by reference numeral 70 is the peak for the ultraviolet absorbtivity of WS 3® having the structure:

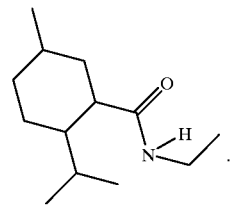

FIG. 7A is an enlargement of section "A" of FIG. 7.

In FIG. 8A, the peak indicated by reference numeral 80 is the peak for the ultraviolet absorbants of the mixture of dimethyl sulfoxide and menthyl glutarates at a pH of 10 in the aqueous phase. In FIG. 8B, the peak indicated by reference numeral 82 is the peak for the ultraviolet absorbtivity at a pH of 10 of dimethyl sulfoxide alone. In FIG. 8C, the peak indicated by reference numeral 84 is the peak for the ultraviolet absorbtivity for menthyl glutarates at a pH of 10, alone.

In the foregoing descriptions of the drawings, when using the term "menthyl glutarates" it is to be understood that "menthyl glutarates" is a 70:30 mixture monomenthyl glutarate having the structure:

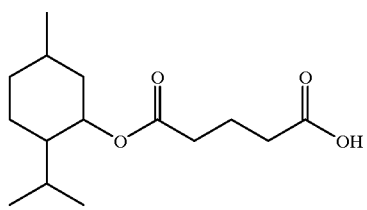

and dimenthyl glutarate having the structure:

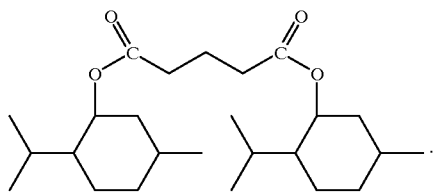

The following examples are given to illustrate embodiments of the invention as it is preferred to practice it. It will be understood that these examples are illustrative, and the invention is not to be considered as restricted thereto, except as indicated in the appended claims.

EXAMPLE I

Oral Hygiene Flavor Formulation

The following basic oral hygiene flavor formulation is prepared:

| Ingredients | Parts by Weight |
| --- | --- |
| Peppermint oil | 89.0 |
| Spearmint oil | 2.0 |
| Clove oil | 1.0 |
| Anethol | 2.0 |
| Cardamom oil | 0.1 |
| Wintergreen oil | 5.0 |
| Cinnamic aldehyde | 0.9 |
| Aspartame having the structure: | 0.05 |

The basic oral hygiene flavor formulation is now divided into two parts. To the first part, a 1:50 mixture of dimethyl sulfoxide:menthyl succinate having the structure:

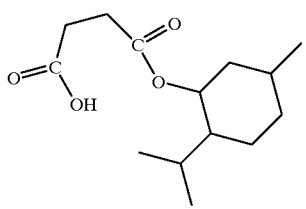

is added at the rate of 10%. To the second part, nothing is added. The flavor with the addition of the dimethyl sulfoxide:menthyl succinate mixture gives rise to a fresher, sweet, licorice, anise oil, spicy aroma and taste characteristics with aesthetically pleasing "cooling" nuances. The peppermint characteristics also appear to be enhanced. The flavor without the dimethyl sulfoxide:menthyl succinate mixture has an unpleasant aftertaste, which is not present in the mixture containing the dimethyl sulfoxide:menthyl succinate mixture. Accordingly, the dimethyl sulfoxide:menthyl succinate-containing composition is preferred by a five member bench panel.

EXAMPLE II

Licorice Chewing Stick

A flexible licorice stick is prepared in a standard manner. Prior to hardening at the level of 0.05 ppm, aspartame having the structure:

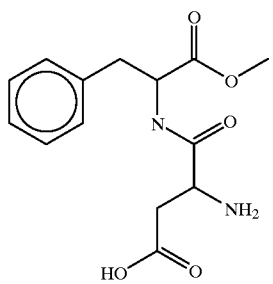

is added to the molten mixture. Also prior to hardening at the level of 6 ppb, a mixture of 2 parts dimethyl sulfoxide:20 parts menthyl lactate is added to the molten mixture. The molten mixture is molded into licorice sticks and hardened for marketing. Each of the licorice sticks has a pleasant, powerful, natural-like licorice anisic, China star anise oil flavor with intense and substantive "cooling" nuances. None of the licorice sticks have a bitter aftertaste. In the absence of the use of the composition which is a mixture of dimethyl sulfoxide and menthyl lactate, each of the licorice sticks, on consumption, does not have any "cooling" nuances imparted in the oral cavity and has a bitter aftertaste. Furthermore, the natural sweetness of each of the licorice sticks is enhanced as a result of the use of the mixture of dimethyl sulfoxide and menthyl lactate.

Preferably, when the dimethyl sulfoxide is admixed with the second sensory perception-affecting compound in order to form the compositions of our invention, the temperature of mixing is between about 15° C. up to about 30° C. at a pressure of from about 0.5 atmospheres up to about 2 atmospheres.

What is claimed is:

1. An oral sensory perception-imparting consumable article having intensified and substantive oral sensory perception-imparting properties, which is an ultimate product selected from the group consisting of beverages, toothpastes, throat lozenges, hard candies, mouthwashes, dental floss, chewing gums, edible films and chewable pharmaceutical products comprising:
   (i) an ultimate product base and intimately admixed therewith
   (ii) dimethyl sulfoxide and at least one second compound selected from the group consisting of:
      (a) a compound containing at least one menthyl moiety;
      (b) a compound containing at least one vanillyl moiety; and
      (c) a compound containing at least one carboxamide moiety
wherein the weight ratio of second compound:dimethyl sulfoxide, is in the range of from about 1,000:1 down to about 3:10 and food grade acceptable salts thereof and further wherein the concentration of dimethyl sulfoxide based on the weight of ultimate product is from about 0.05 up to about 200 ppm, and the concentration of second compound is from about 2 up to about 10,000 ppm on a premixed basis.

2. An oral sensory perception-imparting beverage comprising an aqueous beverage base and admixed therewith in a sensory perception-imparting quantity and concentration, the composition of claim 1.

3. An oral sensory perception-imparting chewing gum comprising a chewing gum base and admixed therewith in an oral sensory perception-imparting quantity and concentration, the composition of claim 1.

4. An oral sensory perception-imparting composition having intensified and substantive oral sensory perception properties consisting essentially of a product produced by the step of admixing dimethyl sulfoxide having the structure:

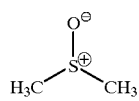

with at least one second compound having a formula selected from the group consisting of:

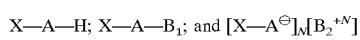

wherein in the weight ratio of second compound:dimethyl sulfoxide, is from 1,000:1 up to 3:10; wherein the step of admixing is carried out at a temperature of from 15° C. up to 30° C. at a pressure of from about 0.5 up to about 2 atmospheres; and wherein X is a menthyl moiety having the structure:

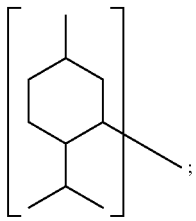

a vanillyl moiety having the structure:

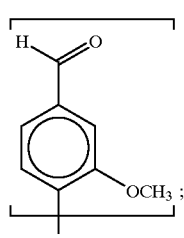

a menthoxy maleyl, glutaryl or succinyl moiety defined according to the structure:

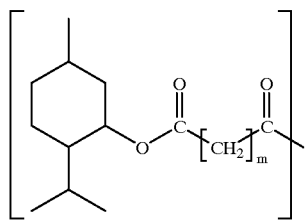

wherein m is an integer of from 1 up to 4;

a menthoxy lactyl moiety having the structure:

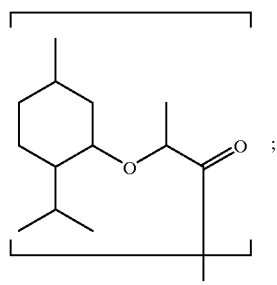

a 2,4-dimethyl-3-hexyl moiety having the structure:

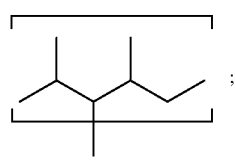

a 2,3,4-trimethyl-3-pentyl moiety having the structure:

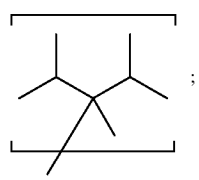

a moiety having the structure:

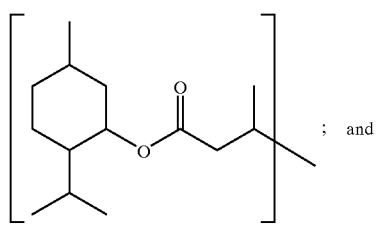

; and a moiety having the structure:

$$\left[ \begin{array}{c} \text{menthyl-CH(NHC}_2\text{H}_5)- \end{array} \right]$$

wherein A is a divalent ether oxygen moiety or alcohol oxygen moiety having the structure: ―)O(― or a divalent carbonyl moiety having the structure:

$$\left[ \begin{array}{c} O \\ \parallel \\ C \end{array} \right]$$

selected from the group consisting of:

$$\left[ \begin{array}{c} R \\ | \\ N \\ | \\ H \end{array} \right]; \quad \left[ -CH_2-\underset{OH}{\underset{|}{C}}H-\underset{OH}{\underset{|}{C}}H-H \right];$$

$$\left[ -(CH_2)_n- \right]; \text{ and}$$

$$\left[ \begin{array}{c} \text{dioxolane-phenyl}(R_{11}, R_{12}, R_{13}) \end{array} \right]$$

wherein $R_{11}$, $R_{12}$ and $R_{13}$ are each the same or different hydrogen or $C_1$–$C_3$ lower alkyl; wherein the concentration of dimethyl sulfoxide based on the weight of ultimate product is from about 0.05 up to about 200 ppm and the concentration of second compound based on the weight of ultimate product is from about 2 up to about 10,000 ppm on a premixed basis; and wherein $B_2$ is a cation selected from the group consisting of:

[$NH_4^+$]; [$Ca^{++}$]; [$Na^+$]; [$Mg^{++}$]; and/or [$K^+$]

and N is an integer of 1 or 2.

5. An oral sensory perception-imparting consumable article having intensified and substantive oral sensory perception-imparting properties, which is an ultimate product selected from the group consisting of beverages, toothpastes, throat lozenges, hard candies, mouthwashes, dental floss, chewing gums, edible films and chewable pharmaceutical products comprising:
  (i) an ultimate product base and intimately admixed therewith
  (ii) the composition of claim 4
wherein the concentration of dimethyl sulfoxide based on the weight of ultimate product is from about 0.05 up to about 200 ppm, and the concentration of second compound is from about 2 up to about 10,000 ppm on a premixed basis.

6. A complex having a structure selected from the group consisting of:

$$\begin{array}{cc} X\!-\!\!A^{\ominus}\!\!-\!\!B_1^{\oplus} & X\!-\!\!A^{\oplus}\!\!-\!\!B_1^{\ominus} \\ H_3C\diagdown \!\!\underset{H_3C}{\overset{|}{S^{\oplus}}}\!\!-\!\!O^{\ominus}; & O^{\ominus}\!\!-\!\!\underset{CH_3}{\overset{|}{S^{\oplus}}}\!\!\diagup CH_3 \end{array} \text{ and}$$

$$\left[ \begin{array}{c} X\!-\!\!A^{\ominus} \\ H_3C\diagdown \!\!\underset{H_3C}{\overset{|}{S^{\oplus}}}\!\!-\!\!O^{\ominus} \end{array} \right]_N \left[ B_2^{+N} \right]$$

wherein X is a menthyl moiety having the structure:

$$\left[ \text{menthyl} \right];$$

a vanillyl moiety having the structure:

$$\left[ \text{4-OCH}_3\text{-3-CHO-phenyl-CH}_2 \right];$$

a menthoxy maleyl, glutaryl or succinyl moiety defined according to the structure:

$$\left[ \text{menthyl-O-C(=O)-[CH}_2]_m\text{-C(=O)-} \right]$$

wherein m is an integer of from 1 up to 4;

a menthoxy lactyl moiety having the structure:

$$\left[ \text{menthyl-O-CH(CH}_3)\text{-C(=O)-} \right];$$

a 2,4-dimethyl-3-hexyl moiety having the structure:

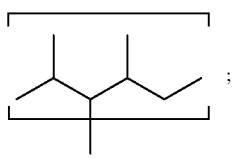

a 2,3,4-trimethyl-3-pentyl moiety having the structure:

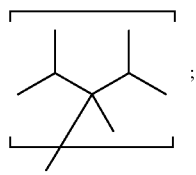

a moiety having the structure:

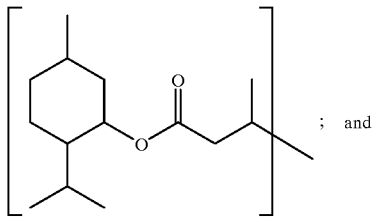

; and a moiety having the structure:

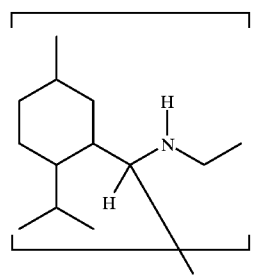

wherein A is a divalent ether moiety having the structure: $-[O]-$ or a divalent carbonyl moiety having the structure:

selected from the group consisting of:

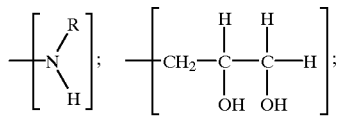

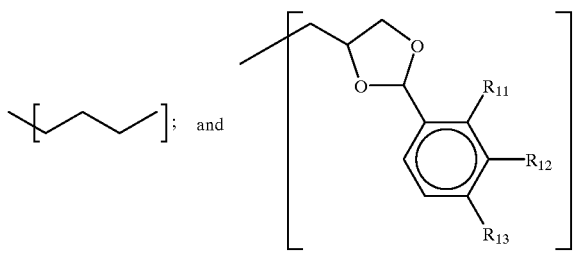

wherein $R_{11}$, $R_{12}$ and $R_{13}$ are each the same or different hydrogen or $C_1$–$C_3$ lower alkyl; wherein the concentration of dimethyl sulfoxide based on the weight of ultimate product is from about 0.05 up to about 200 ppm and the concentration of second compound based on the weight of ultimate product is from about 2 up to about 10,000 ppm on a premixed basis; and; and wherein $B_2$ is a cation selected from the group consisting of:

$[NH_4^+]$; $[Ca^{++}]$; $[Na^+]$; $[Mg^{++}]$; and/or $[K^+]$ and N is an integer of 1 or 2.

* * * * *